(12) United States Patent
Lynch et al.

(10) Patent No.: US 8,686,046 B2
(45) Date of Patent: Apr. 1, 2014

(54) COMPOSITIONS AND METHODS FOR INHIBITING SPHINGOSINE KINASE

(75) Inventors: Kevin R. Lynch, Charlottesville, VA (US); Timothy L. Macdonald, Charlottesville, VA (US); Yugesh Kharel, Charlottesville, VA (US); Thomas P. Mathews, San Diego, VA (US); Brian R. Wamhoff, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 607 days.

(21) Appl. No.: 12/896,881

(22) Filed: Oct. 2, 2010

(65) Prior Publication Data

US 2011/0106241 A1    May 5, 2011

Related U.S. Application Data

(63) Continuation of application No. PCT/US2009/039334, filed on Apr. 2, 2009.

(60) Provisional application No. 61/041,838, filed on Apr. 2, 2008.

(51) Int. Cl.
*A61K 31/175* (2006.01)
*C07C 257/14* (2006.01)

(52) U.S. Cl.
USPC .......................................... 514/617; 564/171

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 2003/0149053 A1 * | 8/2003 | Edney et al. | ............. 514/255.06 |
| 2004/0034075 A1 | 2/2004 | Smith et al. | |

FOREIGN PATENT DOCUMENTS

WO    WO 2005090291 A1 *  9/2005  ............ C07C 257/00
WO    2009/146112 A1    12/2009

OTHER PUBLICATIONS

Ueda et al. Chemical & Pharmaceutical Bulletin, 1968,16(12), 2355-2361.*
Uchida et al. Chemical & Pharmaceutical Bulletin, 1974,7(7), 1720-1721.*
Balthasar et al., "Sphingosine 1-phosphate receptor expression profile and regulation of migration in human thyroid cancer cells," Biochem. J. 398:547-556 (2006).
Berdyshev et al., "Quantitative analysis of sphingoid base-1-phosphates as bis-acetylated derivatives by liquid chromatography-tandem mass spectrometry," Ana. Biochem. 339:129-136 (2005).
Kharel et al., "Sphingosine Kinase 2 is Required for Modulation of Lymphocyte Traffic by FTY720," J. Bio. Chem. 280:36865-36872 (2005).
Park et al., "S1P stimulates chemotactic migration and invasion in OVCAR3 ovarian cancer cells," Biochem. Biophys. Res. Commun. 356:239-244 (2007).
Uchida et al., "Reaction of 2-Benzoylamino-2-methylpropionamidine and 2-Benzoylanninoacetamidine with Bifunctional Compounds," Bulletin of the Chem. Soc. Jap. 47(7):1720-1723 (1974).
International Search Report for PCT/US2009/039334 dated Oct. 1, 2009.
International Preliminary Report on Patentability for PCT/US2009/039334 dated Oct. 5, 2010.

* cited by examiner

*Primary Examiner* — Wu-Cheng Winston Shen
*Assistant Examiner* — Ana Z Muresan
(74) *Attorney, Agent, or Firm* — J. A. Lindeman & Co., PLLC

(57) ABSTRACT

Amidine analogs that can inhibit the activity of sphingosine kinase 1 and sphingosine kinase 2 (SphK1 & SphK2) are provided. The compounds can prevent angiogenesis in tumor cells.

20 Claims, 16 Drawing Sheets

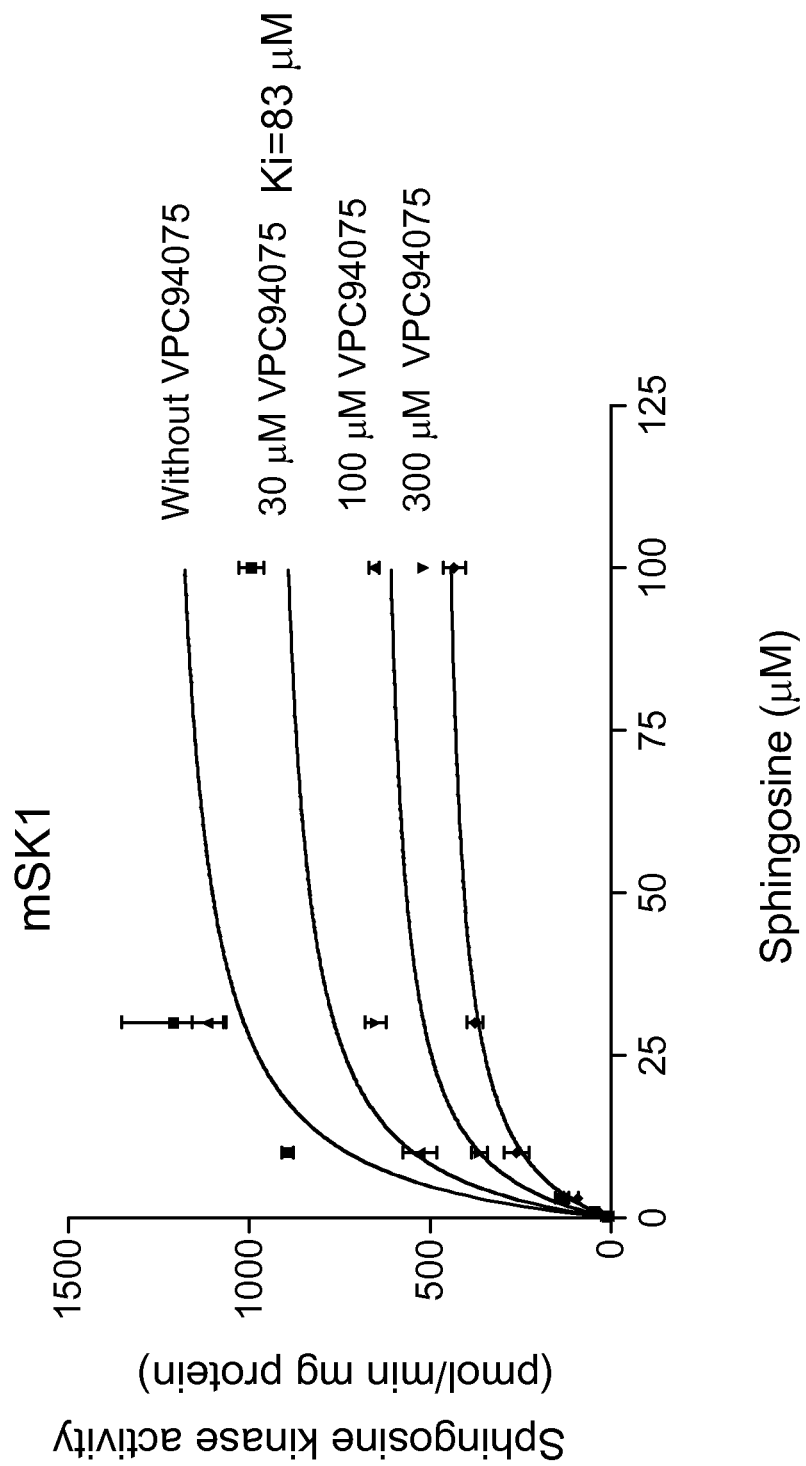

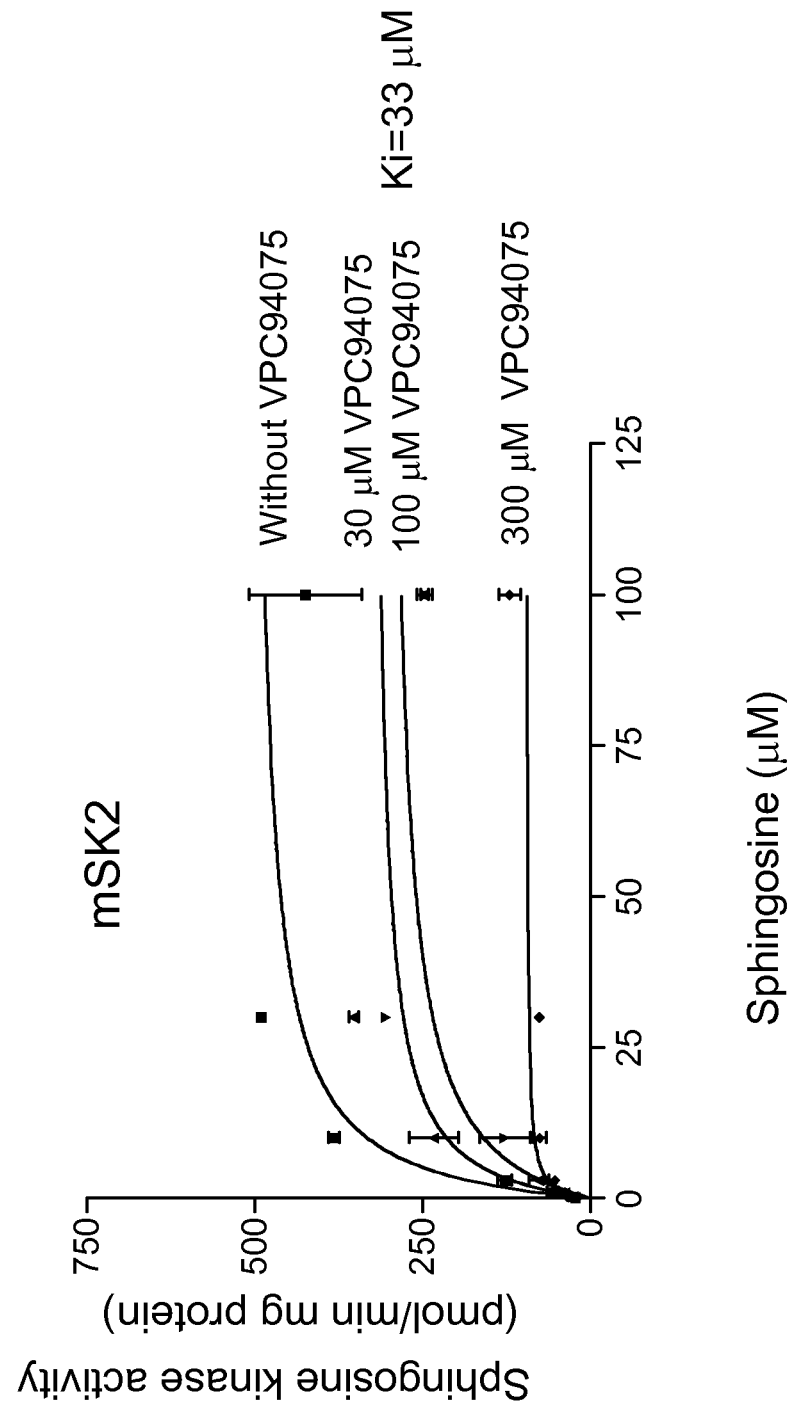

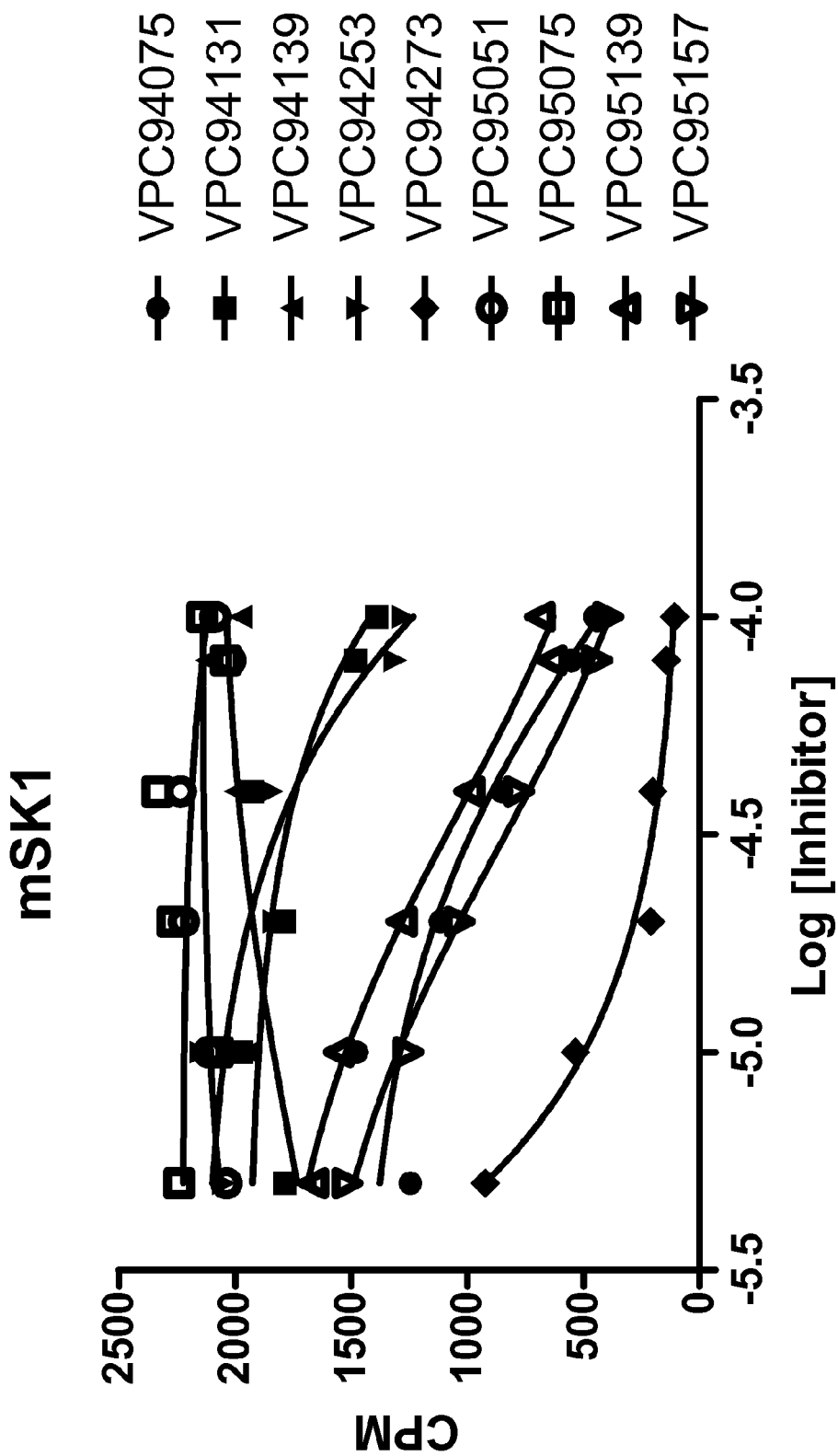

mSK2

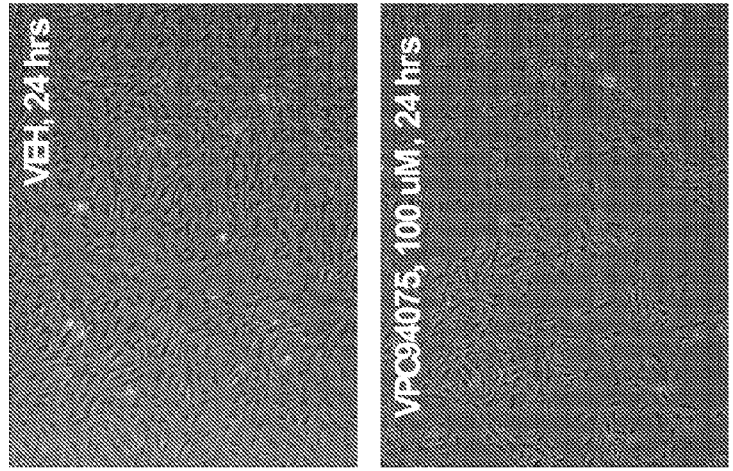
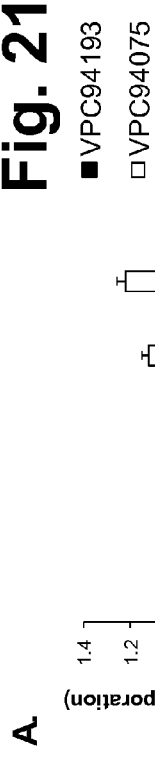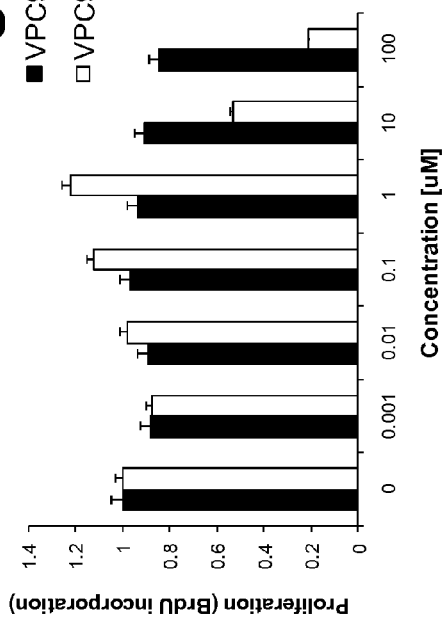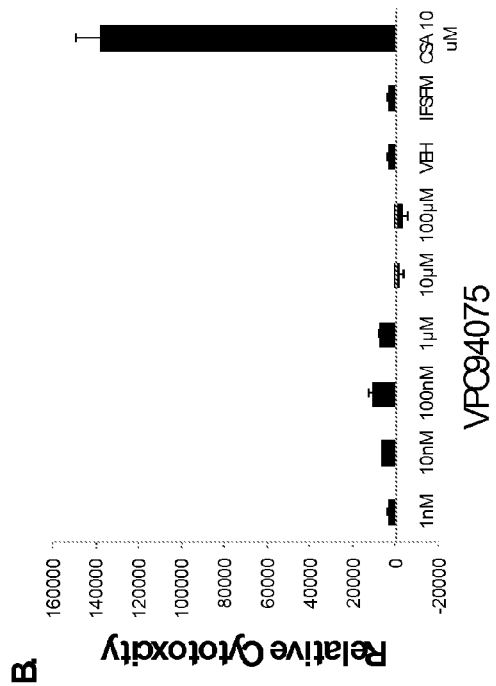
Fig. 21

COMPOSITIONS AND METHODS FOR INHIBITING SPHINGOSINE KINASE

CROSS-REFERENCE TO RELATED APPLICATIONS

This application is a continuation of international application no. PCT/US2009/39334, published as WO 2009/164112 A1, which claims priority to Provisional Application No. 61/041,838, filed Apr. 2, 2008, the disclosures of which are herein incorporated by reference in its entirety.

U.S. GOVERNMENT RIGHTS

This invention is made with United States Government support under Grant Nos. RO1 GM 067958 and RO1 HL081682 awarded by the National Institutes of Health. The United States Government has certain rights in the invention.

BACKGROUND OF THE INVENTION

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{62\ \gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl)ethyl] propane 1,3-diol), that following phosphorylation, is an agonist at 4 of 5 S1P receptors, revealed that enhancing S1P tone influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds.

Sphingosine 1-phosphate (S1P) is a lysophospholipid mediator that evokes a variety of cellular responses by stimulation of five members of the endothelial cell differentiation gene (EDG) receptor family and has been demonstrated to induce many cellular processes, including those that result in platelet aggregation, cell proliferation, cell morphology, tumor-cell invasion, endothelial cell chemotaxis and angiogenesis. For these reasons, S1P receptors and sphingosine kinases are good targets for therapeutic applications such as wound healing and tumor growth inhibition.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

The importance of sphingosine kinase 1 and 2 (SphK1 & SphK2) in cell growth and proliferation has also been recognized. SphK1 & 2 catalyze the phosphorylation of the endogenous lipid D-erythro sphingosine to sphingosine 1-phosphate (S1P). SphK1 & 2 are also responsible for the equilibrium between the anti-apoptotic S1P and its pro-apoptotic metabolic precursor ceramide. Thus, SphK1 & 2 have been proposed to be important drug targets. However, only a small number of compounds have been shown to inhibit the sphingosine kinases, including DL-threo-dihydrosphingosine, N,N-dimethylsphingosine and short-chain DL-erythro-sphingosine analogues. However, these compounds are not suitable as in vivo inhibitors and cannot address questions concerning SphK mediated disease states.

Traditional methods of inhibiting sphingosine kinase have centered on targeting the ATP binding site of the kinase, a strategy that has enjoyed moderate success. However, such methods suffer from limited of selectivity across a wide array of kinases. Additionally, the sequence of the ATP binding domain of SphK1 & 2 is highly conserved across a number of diacylglycerol (DAG) kinase family members, rendering the traditional strategy problematic.

Currently, there is a need for novel, potent, and selective agents that inhibit the substrate-binding domain of the sphingosine kinases (e.g., mouse and human SphK1 and SphK2) that have enhanced potency, selectivity, and oral bioavailability. In addition, there is a need in the art for identification of, as well as the synthesis and use of such compounds. The present invention satisfies these needs.

SUMMARY

The present invention provides in one aspect compounds that selectively inhibit S1P kinases. Accordingly, there is provided compounds of Formula IA:

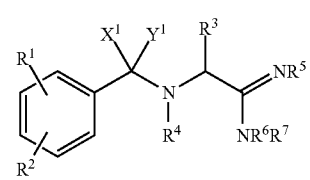

IA wherein $X^1$ and $Y^1$ are independently hydrogen or ($C_1$-$C_4$) alkyl; or $X^1$ and $Y^1$ taken together are O or S;

$R^1$ and $R^2$ are independently hydrogen, halo, halo($C_1$-$C_{10}$) alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$) cycloalkyl, ($C_6$-$C_{10}$)aryl, ($C_7$-$C_{30}$)arylalkyl, ($C_2$-$C_{10}$) heterocyclic, ($C_4$-$C_{10}$)heteroaryl, or ($C_4$-$C_{10}$)heteroaryl($C_1$-$C_{20}$)alkyl; or $R^2$ can be a group having Formula II, III, IV, V, or VI:

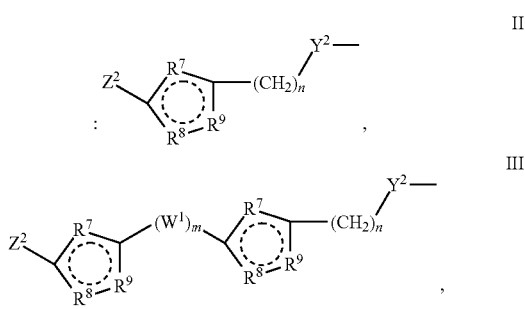

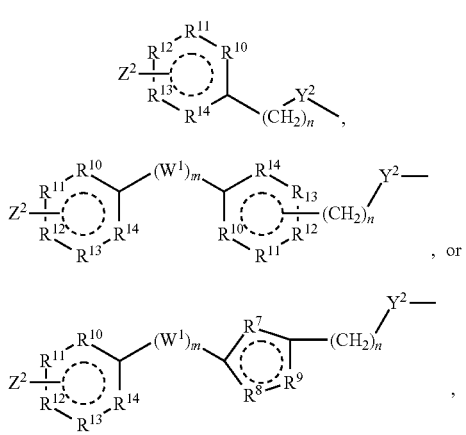

wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{18}$;

each $R^{15}$, $R^{16}$ and $R^{17}$ is independently hydrogen, halo, $(C_1-C_{10})$alkyl, $(C_6-C_{10})$aryl, $(C_1-C_{10})$alkyl substituted with halo, hydroxy, $(C_1-C_{10})$alkoxy, or cyano; and where $R^{18}$ can be hydrogen or $(C_1-C_{10})$alkyl;

$Z^2$ is hydrogen, halo, halo$(C_1-C_{10})$alkyl, cyano, $-NR^cR^d$, $(C_1-C_{20})$alkyl, $(C_2-C_{20})$alkenyl, $(C_2-C_{20})$alkynyl, $(C_1-C_{20})$alkoxy, $(C_2-C_{26})$alkoxyalkyl, $(C_3-C_{12})$cycloalkyl, $(C_6-C_{10})$aryl, $(C_7-C_{30})$arylalkyl, $(C_2-C_{10})$heterocyclic, $(C_4-C_{10})$heteroaryl, or $(C_4-C_{10})$heteroaryl$(C_1-C_{20})$alkyl. The alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, $(C_1-C_{10})$alkoxy, $C_6$-aryl, $(C_7-C_{24})$arylalkyl, oxo (=O), or imino (=$NR^f$), wherein one or more of the carbon atoms in the $Z^2$ alkyl groups can be independently replaced with non-peroxide oxygen, sulfur or $NR^e$;

indicates one or more optional double bonds;

$Y^2$ is a bond, O, S, C=O, or $NR^e$, $CH_2$; $W^1$ is a bond, $-CH_2-$ and m is 1, 2, or 3, or (C=O)$(CH_2)_{1-5}$ and m is 1; wherein $W^1$ is optionally interrupted with non-peroxide O, S, C=O, or $NR^e$; and n is 0, 1, 2, or 3.

$R^3$ is hydrogen, $(C_1-C_4)$alkyl, hydroxy$(C_1-C_3)$alkyl, $(C_1-C_3)$alkoxy or halo$(C_1-C_3)$alkyl; and each $R^4$, $R^5$, $R^6$ and $R^7$ are independently hydrogen, $(C_1-C_4)$alkyl or halo$(C_1-C_3)$alkyl.

The alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, $(C_1-C_{10})$alkoxy, $C_6$-aryl, $(C_7-C_{24})$arylalkyl, oxo (=O), or imino (=$NR^f$), wherein one or more of the carbon atoms in the $R^1$ or $R^2$ alkyl groups can be independently replaced with non-peroxide oxygen, sulfur or $NR^e$. Each of $R^a$, $R^b$, $R^c$, $R^d$, $R^e$ and $R^f$ is independently hydrogen, or $(C_1-C_{10})$alkyl. The invention includes pharmaceutically acceptable salts or esters of the compounds of Formula IA.

In another aspect, the present invention provides a method for inhibiting angiogenesis in a tumor, including contacting the cancerous cells with an effective amount of a compound of Formula IA, or a pharmaceutically acceptable salt or ester thereof.

In another aspect, the present invention provides a method for preventing or treating diseases that involve excess vascular growth, e.g. retinal degenerative diseases such as macular degeneration, comprising contacting the affected area with an effective amount of the compound of Formula IA. For example the compound can be injected into the posterior eye in depot form.

In another aspect, the invention provides a method for repairing a vascular injury following catheterization, including contacting the lumen of the affected vessel with an effective amount of the compound of Formula IA. In another aspect, the invention includes coating indwelling stents with a compound of Formula IA.

In another aspect, the present invention provides compositions and methods for the use of SphK inhibitors to prevent and inhibit vascular restenosis following vascular injury. For example, the injury can be due to balloon angioplasty. In another aspect, the present invention includes a method for treating subjects to prevent vascular restenosis.

In another aspect, the present invention provides compositions and methods for the use of SphK inhibitors to prevent asthma attacks. In one aspect, the asthma could be due to over production of cysteinyl leukotrienes. In another aspect, the present invention includes a method for treating subjects suffering from asthma.

In another aspect, the present invention provides compositions and methods for the use of SphK inhibitors for the treatment of neoplastic disease. In one aspect, this treatment is effected by application of SphK inhibitors that are efficacious by virtue of their anti-angiogenic properties.

In another aspect, the invention provides a method for parenteral delivery of a compound of formula IA prior to and/or following intravascular stenting.

In another aspect, the invention provides an angioplasty balloon catheter for vessel dilatation prior to direct stent delivery coated with of a compound of Formula IA. The compound of Formula IA is delivered to the diseased vessel wall by direct contact of the angioplasty balloon surface with the vessel wall.

In another aspect, the present invention provides a metal stent coated directly on the surface with of a compound of Formula IA. The compound of Formula IA is delivered to the stented vessel wall by direct contact of the stent struts with the vessel wall.

In another aspect, the present invention provides a compound of Formula IA is incorporated into a non-degradable polymer or co-polymer, such as but not restricted to polyethylene-co-vinyl acetate (PEVA) and poly n-butyl methacrylate, and coating a bare metal stent with the polymer.

In another aspect, the present invention provides a compound of Formula IA is incorporated into a biodegradable polymer or co-polymer, such as but not limited to poly lactic acid glycolic acid (PLGA) or phosphorylcholine, and coating a bare metal stent with the polymer. The compound of Formula IA is delivered to the stented vessel wall by elution from the biodegradable polymeric surface on the stent.

In another aspect, the present invention provides a compound of Formula IA incorporated into a stent device that contains a nanoporous surface modification, such as but not limited to a ceramic, metal or other material coated on the bare metal stent as a nanoporous surface modification. The compound of Formula IA is delivered to the stented vessel wall by elution from the nanoporous surface.

In another aspect, the present invention provides a compound of Formula IA incorporated into a stent device that contains a microporous surface modification, such as but not limited to a ceramic, metal or other material coated on the bare metal stent as a microporous surface modification. The compound of Formula IA is delivered to the stented vessel wall by elution from the microporous surface.

In another aspect, the present invention provides a non-metallic biodegradable or non-degradable stent device combined with a compound of Formula IA. The compound of Formula IA is delivered to the stented vessel wall by elution from the non-metallic biodegrable or non-biodegradable stent matrix.

In another aspect, the invention provides a compound of Formula IA, a pharmaceutically acceptable salt or ester thereof for use in medical treatment (for example, treatment of neoplastic disease.

In another aspect, the invention provides a method for the use of a compound of Formula IA or a pharmaceutically acceptable salt or ester thereof to prepare a medicament for inhibiting tumor growth, metastasis or tumor angiogenesis in a mammalian species (for example, a human).

In another aspect, the invention provides for the use of a compound of Formula IA or a pharmaceutically acceptable salt or ester thereof to prepare a medicament for repairing a vascular injury following catheterization. In another aspect, the invention includes use of a compound of Formula IA for coating indwelling stents.

In another aspect, the invention provides novel intermediates and processes disclosed herein that are useful for preparing compounds of Formula IA, including the generic and specific intermediates as well as the synthetic processes described herein.

In another aspect, the present invention provides synthetic schemes and methods of use of compounds having Formula IA and analogs or derivatives thereof. In another aspect, the invention provides synthetic and modification schemes for preparing analogs and derivatives of the compounds of Formula IA, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

BRIEF DESCRIPTION OF THE DRAWINGS

FIGS. 14 and 15 illustrate the results of the in vitro sphingosine kinase assay.

FIGS. 16 and 17 illustrate the results of the in vitro Sphingosine Kinase Competition Assay using the disclosed compounds.

FIGS. 21A, 21B, and 21C illustrate the prevention of PDGF-BB-induced SMC proliferation using the disclosed compounds.

DETAILED DESCRIPTION

Figure 1:
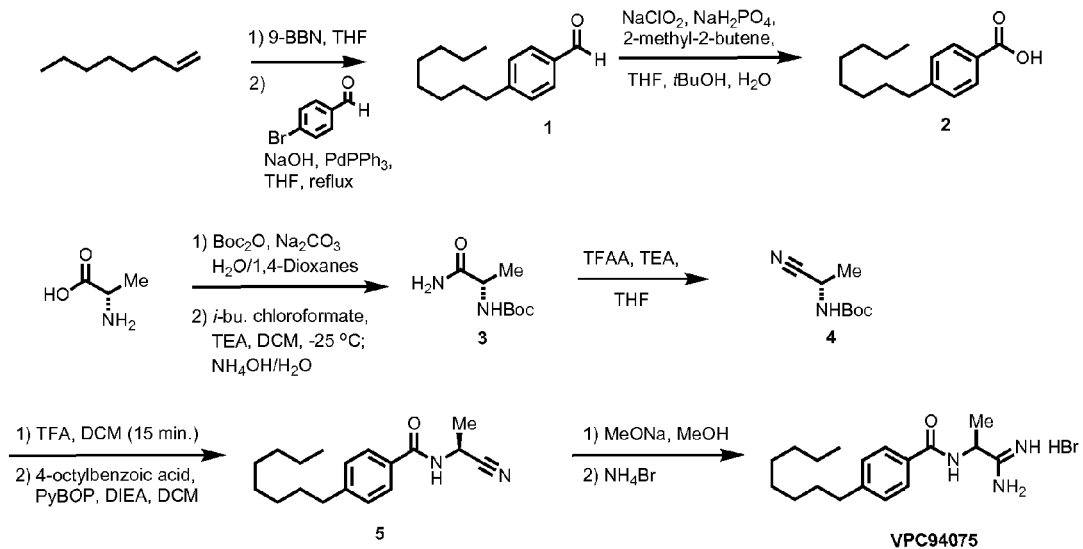
FIGS. 1-12 illustrate syntheses of compounds of Formula IA.
Figure 2:
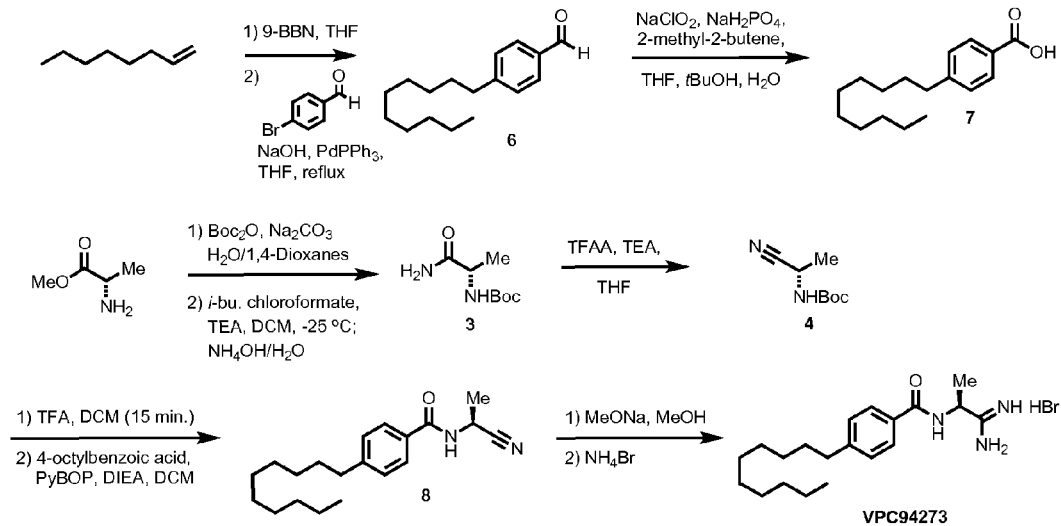
Figure 3:
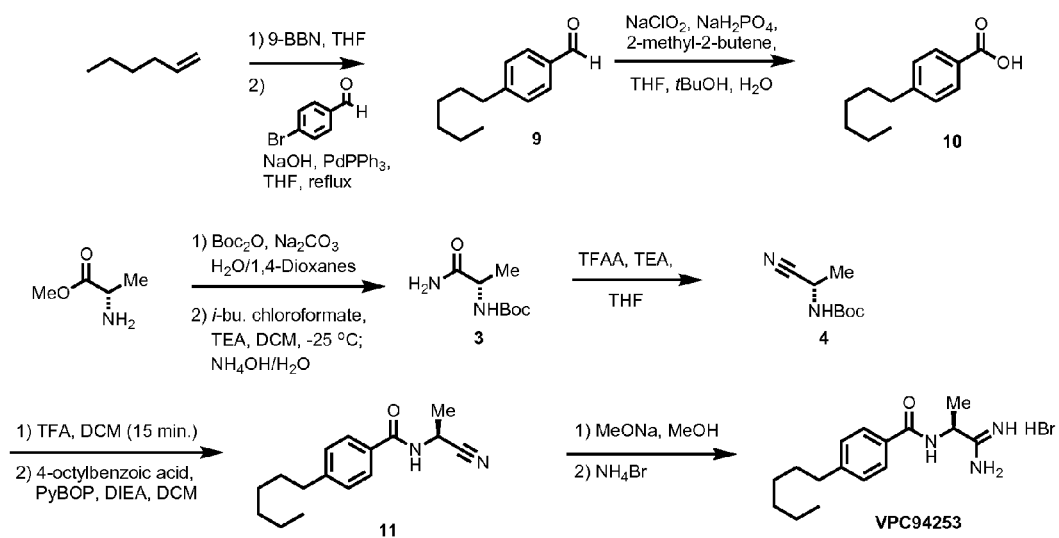
Figure 4:
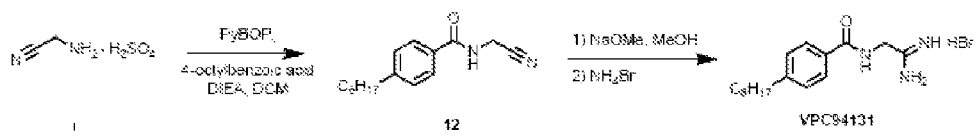
Figure 5:
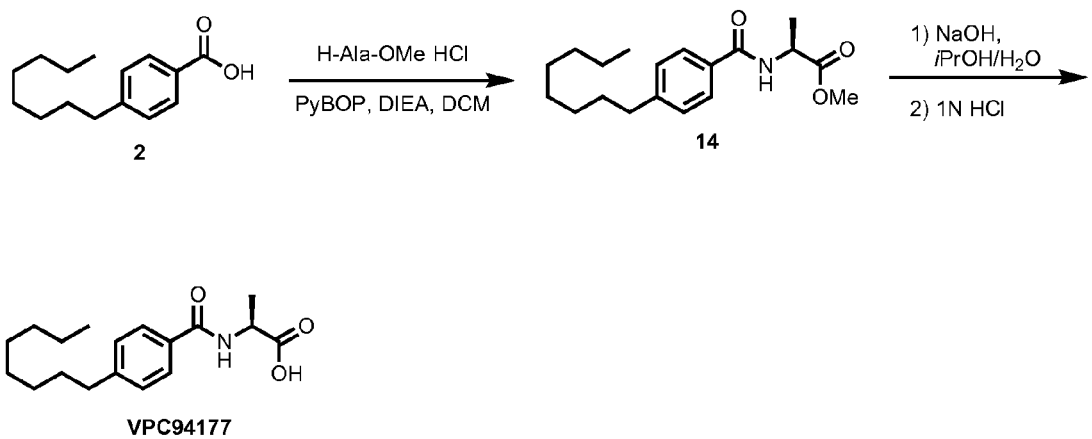
Figure 6:
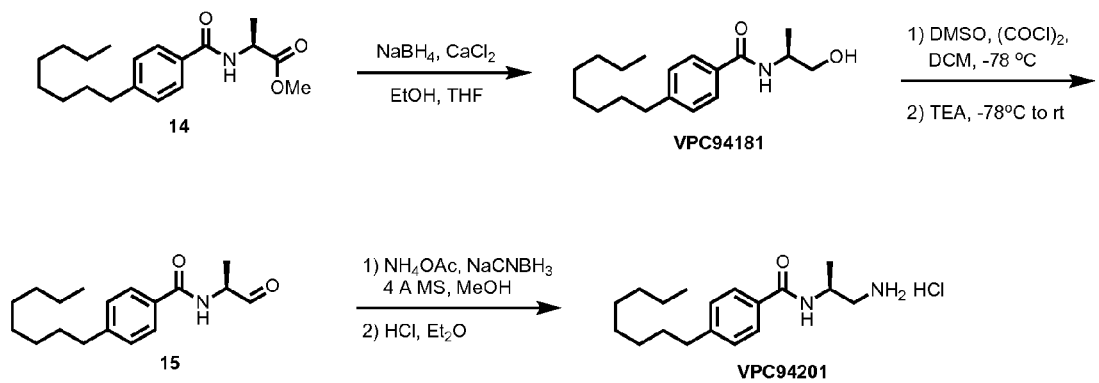
Figure 7:
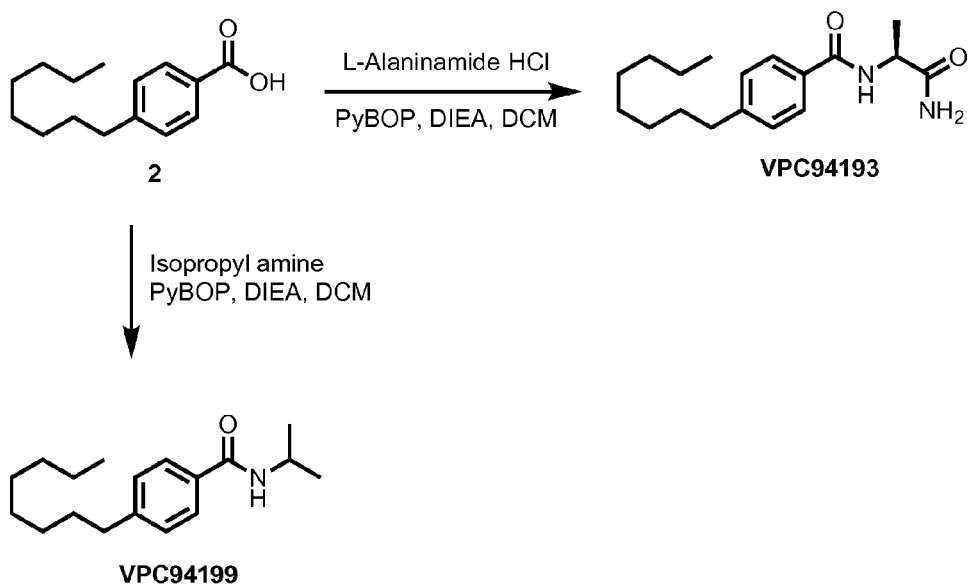
Figure 8:
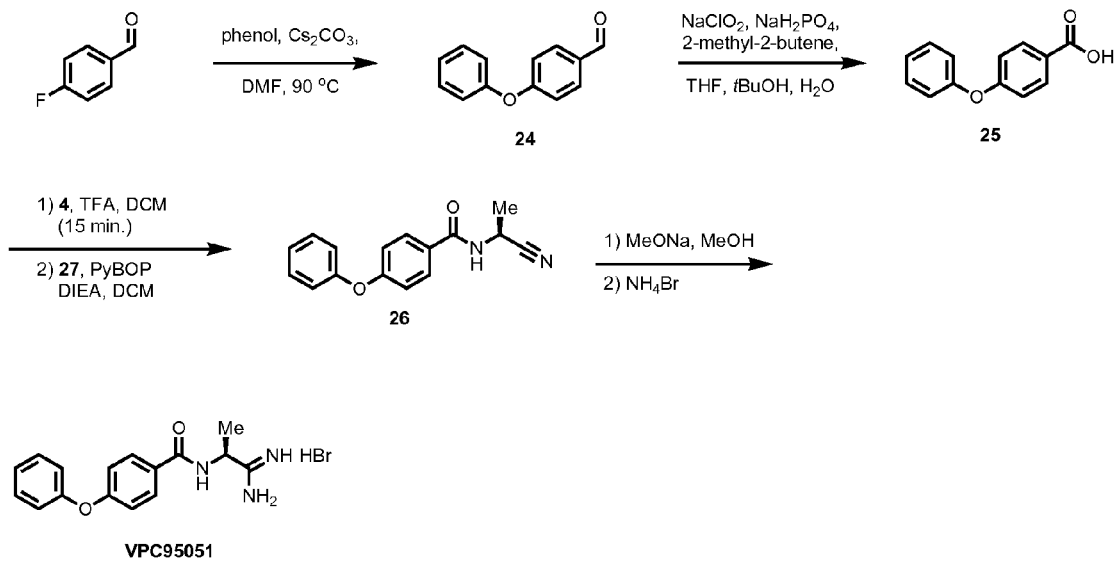
Figure 9:
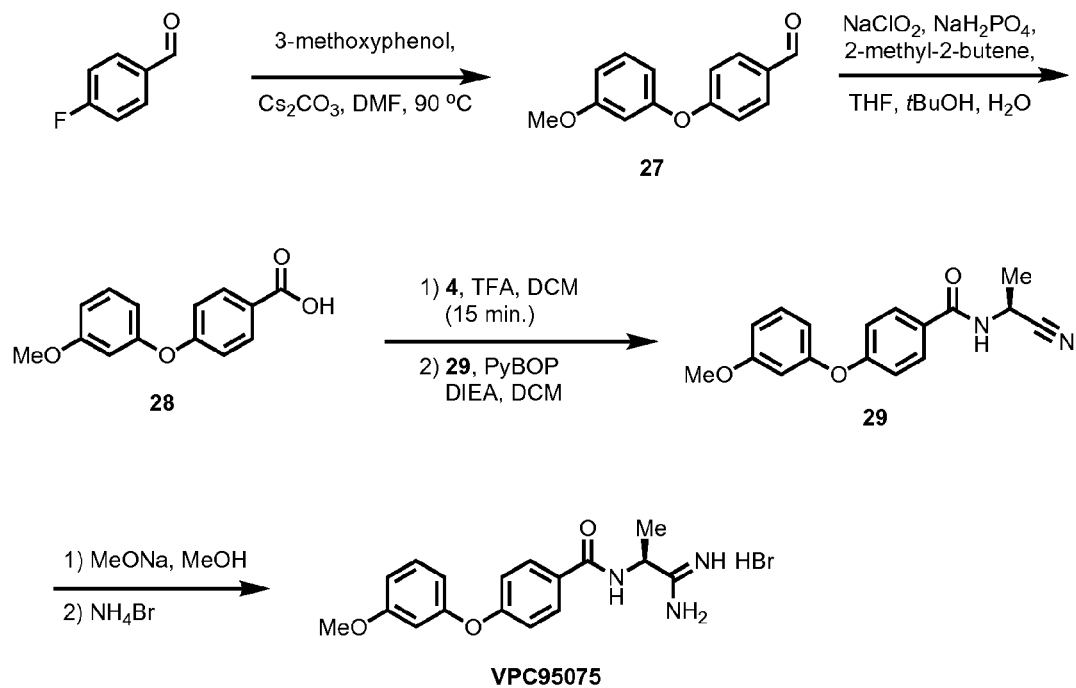
Figure 10:
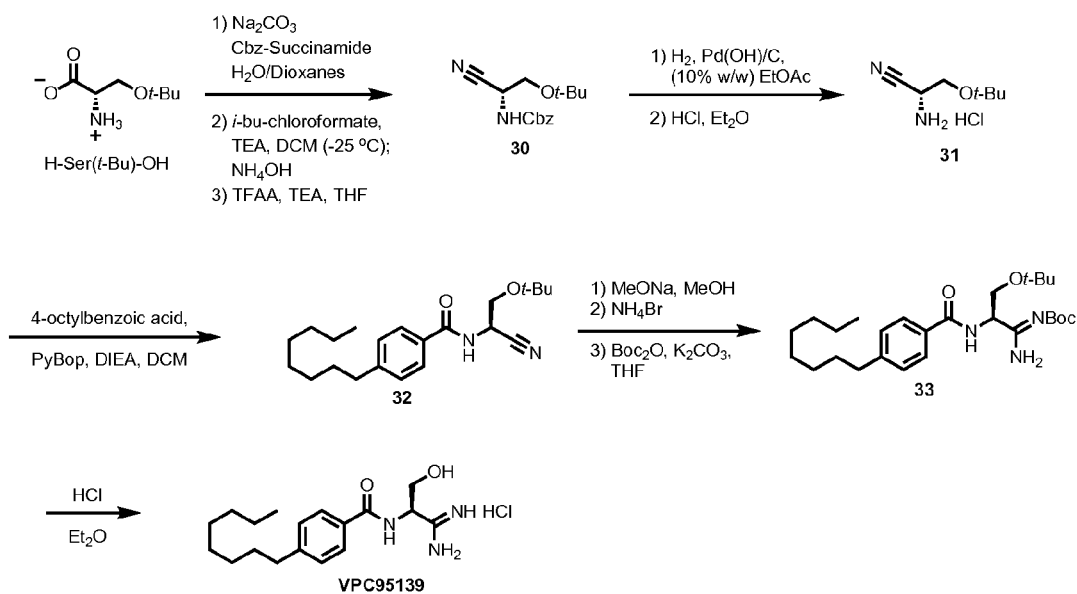
Figure 11:
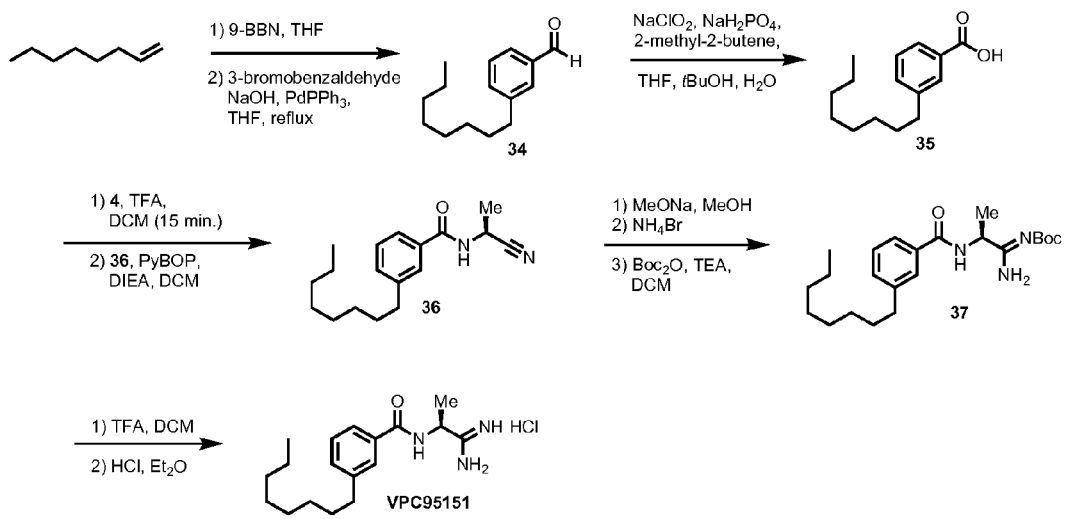
Figure 12:
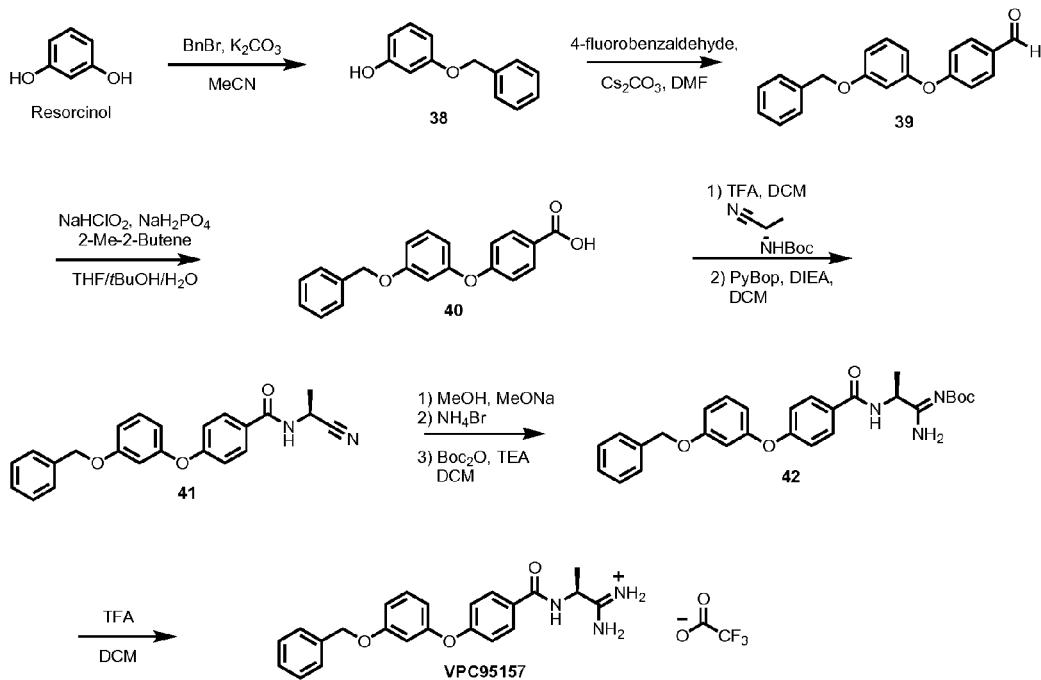
Figure 13A:
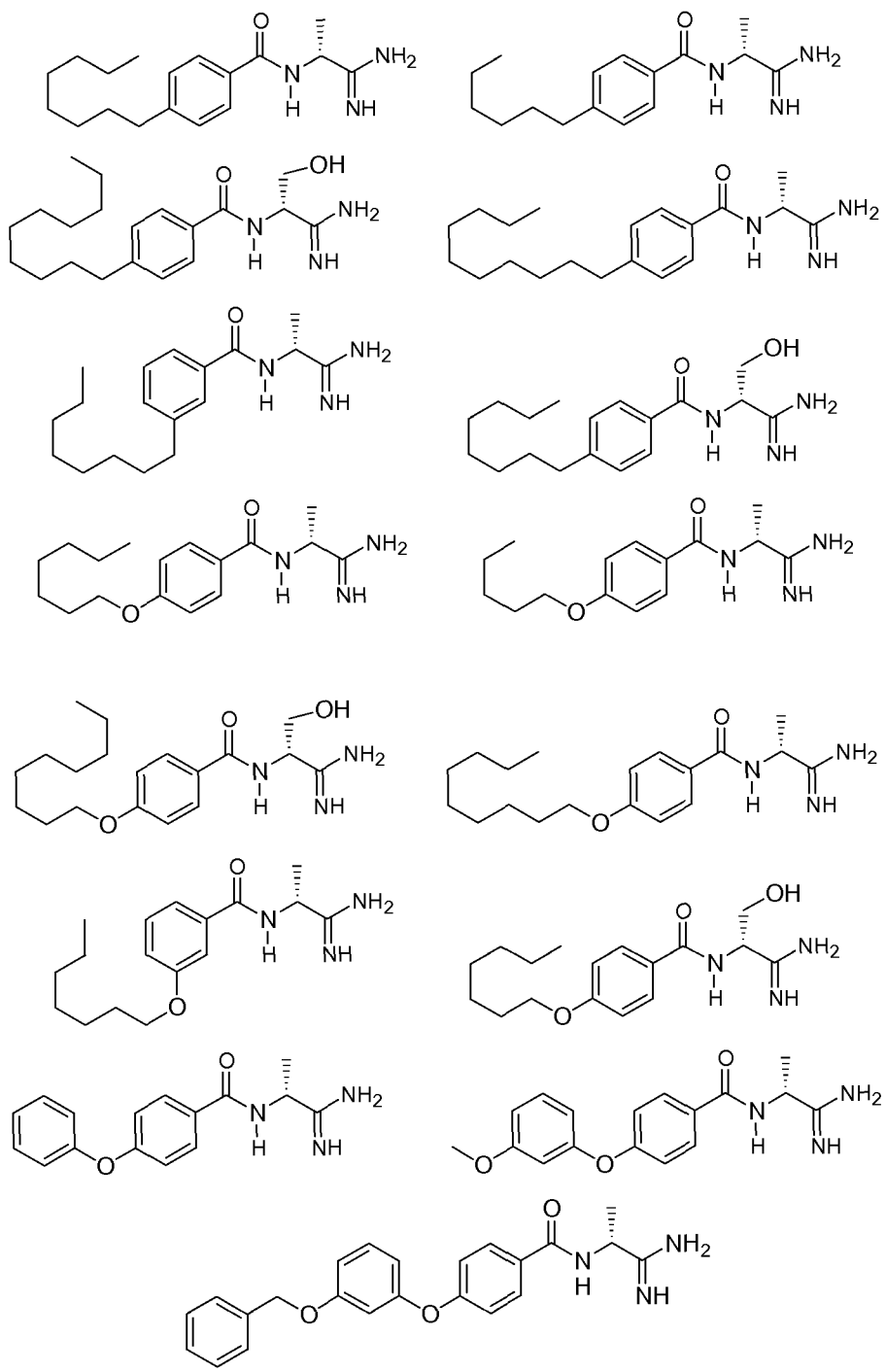
FIGS. 13A and 13B illustrates additional compounds of Formula IA.
Figure 13B:
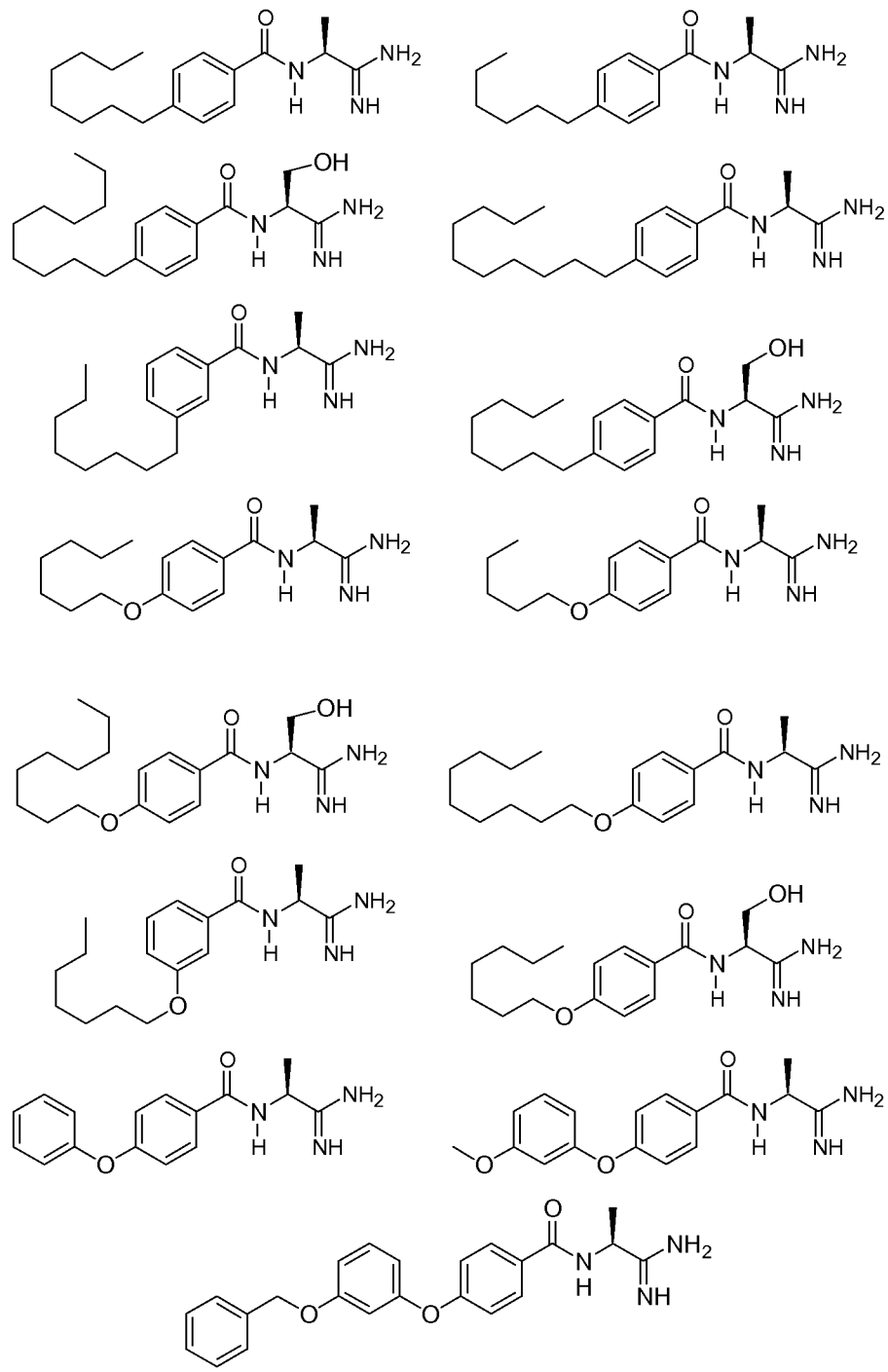

The following abbreviations are used herein: SphK Sphingosine kinase (types 1 and 2), S1P sphingosine 1-phosphate, SMC smooth muscle cell, BrdU bromodeoxyuridine, CsA cyclosporin A In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Exemplary and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "receptor agonists" are compounds that mimic the action of S1P at one or more of its receptors but may have differing potency and/or efficacy.

The term "receptor antagonists" are compounds that 1) lack intrinsic agonist activity and 2) block agonist (e.g., S1P) activation of the S1P receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue is obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an S1P receptor antagonist is an amount that decreases the cell signaling activity of the S1P receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function Inhibition is by at least 10%, preferably by at least 25%, more preferably by at least 50%, even more preferably by at least 75%, and most preferably, the function is inhibited by at least 95%.

"Instructional material" includes a publication, a recording, a diagram, or any other medium of expression which can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "rt" for room temperature, "THF" for tetrahydrofuran, and "rac" for racemic mixture).

The values listed below for radicals, substituents, and ranges, are for illustration only; they do not exclude other defined values or other values within defined ranges for the radicals and substituents. The disclosed compounds include compounds of Formula IA, IB, or IC having any combination of the exemplary values, preferred values, and more preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like. The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The term "($C_1$-$C_{20}$)alkoxy" refers to an alkyl group attached through an oxygen atom. Examples of ($C_1$-$C_{20}$)alkoxy can be methoxy, ethoxy, propoxy, isopropoxy, butoxy, iso-butoxy, sec-butoxy, pentoxy, 3-pentoxy, hexyloxy, heptoxy, or octoxy and the like. The term ($C_2$-$C_{26}$)alkoxyalkyl can be methoxy methyl, methoxy ethyl, ethoxy methyl, ethoxy ethyl, and the like.

The term "$C_3$-$C_{12}$ cycloalkyl", can be cyclopropyl, cyclobutyl, cyclopentyl, cyclohexyl, cycloheptyl, cyclooctyl and the like.

The term "optionally substituted" refers to zero, one, two, three or four substituents, wherein the substituents are each independently selected. Each of the independently selected substituents may be the same or different than other substituents.

The term "($C_6$-$C_{10}$)aryl" refers to a mono or bicyclic carbocyclic ring system having one or two aromatic rings including, but not limited to, phenyl, benzyl, naphthyl, tetrahydronaphthyl, indanyl, indenyl, and the like.

The term "aryl($C_1$-$C_{20}$)alkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, or amino substituents.

The "($C_2$-$C_{10}$)heterocyclic group" refers to an optionally substituted mono- or bicyclic carbocyclic ring system containing one, two, or three heteroatoms (optionally in each ring) wherein the heteroatoms are oxygen, sulfur, and nitrogen.

The term "($C_4$-$C_{10}$)heteroaryl" refers to an optionally substituted mono- or bicyclic carbocyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "bicyclic" represents either an unsaturated or saturated stable bridged or fused bicyclic carbon ring. The bicyclic ring may be attached at any carbon atom which affords a stable structure. Typically a bicyclic ring system can have from about 7 to about 12 atoms in the ring system. The term includes, but is not limited to, naphthyl, dicyclohexyl, dicyclohexenyl, and the like.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

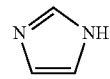

is understood to represent a mixture of the structures:

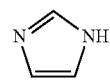

as well as

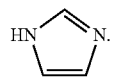

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

The disclosed compounds can contain one or more asymmetric centers in the molecule. In accordance with the present disclosure any structure that does not designate the stereochemistry is to be understood as embracing all the various optical isomers, as well as racemic mixtures thereof.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, resolution of the racemic form by recrystallization techniques, synthesis from optically-active starting materials, chiral synthesis, or by chromatographic separation using a chiral stationary phase) and how to determine S1P agonist activity using the standard tests described herein, or using other similar tests which are well known in the art. In addition, some compounds may exhibit polymorphism.

Potential uses of a SphK inhibitors include, but are not limited to, anti-angiogenesis, treating neoplastic disease, preventing restenosis and treating vascular injury In another aspect, the present invention provides compositions and methods for the use of SphK inhibitors to prevent and inhibit vascular restenosis following vascular injury. In one aspect, the injury can be due to balloon angioplasty. The present invention further provides methods for treating subjects to prevent vascular restenosis.

In another aspect, the present invention provides compositions and methods for the use of SphK inhibitors to prevent asthma attacks. In one aspect, the asthma could be due to over production of cysteinyl leukotrienes. The present invention further provides methods for treating subjects to treat asthma.

In another aspect, the present invention provides compositions and methods for the use of SphK inhibitors for the treatment of neoplastic disease. In one aspect, this treatment is effected by application of SphK inhibitors that are efficacious by virtue of their anti-angiogenic properties.

The present invention also includes pharmaceutical compositions including the disclosed compounds. More particularly, such compounds can be formulated as pharmaceutical compositions using standard pharmaceutically acceptable carriers, fillers, solubilizing agents and stabilizers known to those skilled in the art. For example, a pharmaceutical composition including a disclosed compound, analog, derivative, or modification thereof, as described herein, is used to administer the appropriate compound to a subject.

The compounds of Formula IA and IB are useful for treating a disease or disorder including administering to a subject in need thereof of a therapeutically acceptable amount of a compound of Formula IA, or a pharmaceutical composition comprising a therapeutically effective amount of a compound of Formula IA, and a pharmaceutically-acceptable carrier.

The disclosed compounds and method are directed to SphK inhibitors that have activity as inhibitors of SphK1, SphK2, or both enzymes.

Exemplary and preferred values listed below for radicals, substituents, and ranges, are for illustration only; they do not exclude other defined values or other values within defined ranges for the radicals and substituents.

Exemplary values for $X^1$ and $Y^1$ are independently hydrogen, $CH_3$, or together $X^1$ and $Y^1$ are O.

Values for $R^1$ are hydrogen, fluorine, chlorine, bromine, trifluoro-methyl, methoxy, $(C_1-C_6)$alkyl, $(C_1-C_6)$haloalkyl, or $(C_1-C_6)$alkyl substituted with, alkoxy or cyano.

More values for $R^1$ are hydrogen, trifluoro-methyl, or —$CH_2CF_3$.

Additional values for $R^1$ are alkyl-substituted aryl, aryl-substituted alkyl, or aryl-substituted arylalkyl.

Even more values for $R^1$ are benzyl, phenylethyl, or benzyl substituted with methyl.

Values for $R^2$ include

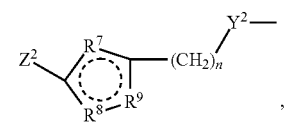

II

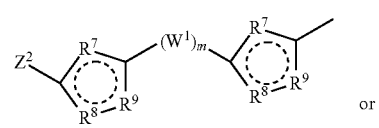

III or

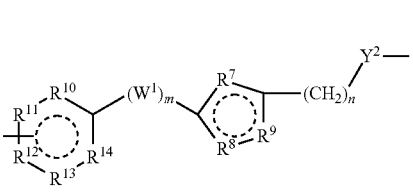

VI

An additional value for $R^2$ is:

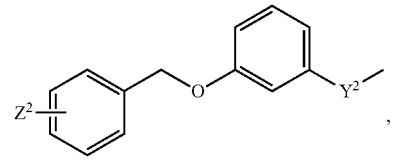

An additional value for $R^2$ is:

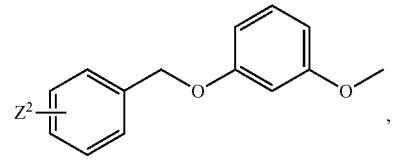

where $Z^2$ is hydrogen or $(C_1-C_{10})$alkyl or $(C_1-C_{10})$alkoxy.

Additional values for $R^2$ having Formula VI are

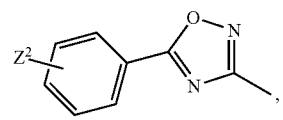

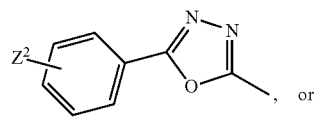, or

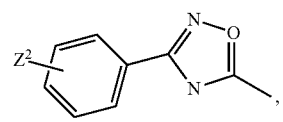

wherein $Z^2$ is $(CH_3)_3C-$, $CH_3CH_2(CH_3)_2C-$, $CH_3CH_2CH_2-$, $CH_3(CH_2)_2CH_2-$, $CH_3(CH_2)_4CH_2-$, $(CH_3)_2CHCH_2-$, $(CH_3)_3CCH_2-$, $CH_3CH_2O-$, $(CH_3)_2CHO-$, or $CF_3CH_2CH_2-$ or a group having the formula:

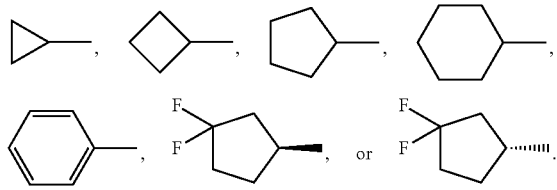

An additional value for $R^2$ having Formula VI (para substituted 3,5-diphenyl-(1,2,4)-oxadiazoles) is;

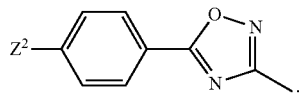

Another value for $R^2$ having Formula VI is;

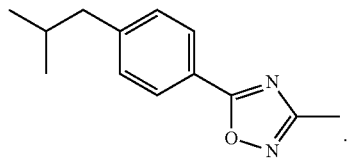 [SMILES: Cc1noc(-c2ccc(CC(C)C)cc2)n1]

Another value for $R^2$ having Formula II is;

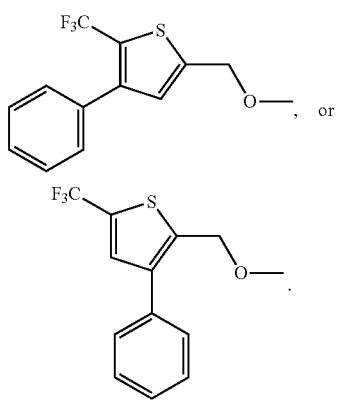

Another exemplary value for $R^2$ having Formula II is;

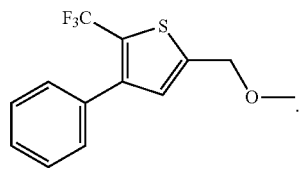 [SMILES: COCc1cc(-c2ccccc2)c(C(F)(F)F)s1]

An exemplary values for $R^2$ having Formula III include;

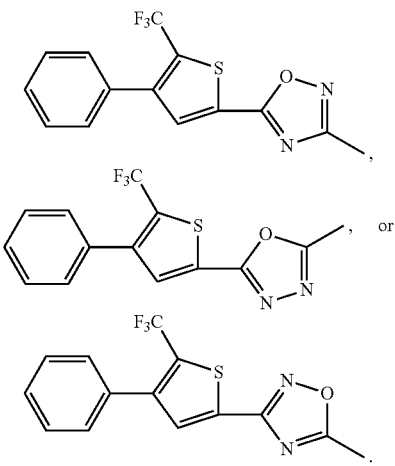

An exemplary value for $R^2$ having formula V is;

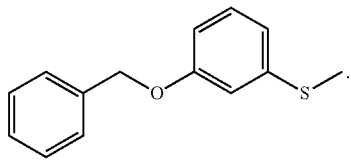 [SMILES: CSc1cccc(OCc2ccccc2)c1]

Additional values for $R^2$ include $(C_1-C_{20})$alkyl, $(C_1-C_{20})$alkoxy, or $(C_2-C_{26})$alkoxyalkyl.

More additional values for $R^2$ include $(C_1-C_{10})$alkyl, $(C_2-C_{10})$alkenyl and $(C_2-C_{14})$alkynyl or $(C_1-C_{10})$alkoxy optionally substituted with carbonyl (C=O) or oxime (C=NR$^d$) groups.

Additional values for $R^2$ include methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

Values for $R^3$ include methyl, hydroxymethyl, ethyl, hydroxyethyl, propyl, hydroxypropyl, or isopropyl.

Additional values for $R^3$ include methyl, hydroxymethyl, ethyl, or hydroxyethyl.

Values for $R^4$ include is hydroxy, or phosphate ($-OPO_3H_2$).

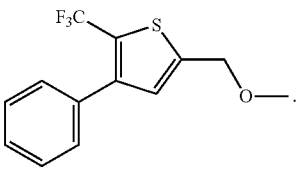 [SMILES: COCc1cc(-c2ccccc2)c(C(F)(F)F)s1]

Exemplary compounds of the invention have formulas

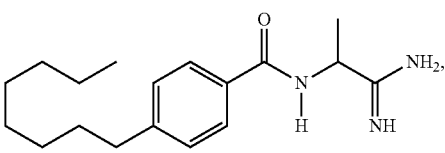

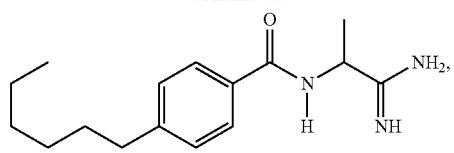
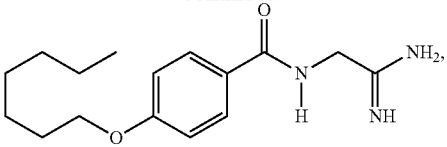

Additional compounds of Formula IA are illustrated in table 1, below.

TABLE 1

| Compound | R^e |
|---|---|

(Structures shown at top of table:)

- Benzamide with R^e substituent, N-H linked to CH(C(=NH)NH_2)
- Benzamide with R^e substituent, N-H linked to CH(CH_2OH)(C(=NH)NH_2)

or

- Benzamide with R^e substituent, N-H linked to CH(H)(C(=NH)NH_2)

| Compound | R^e |
|---|---|
| XX | 4-isobutylphenyl group attached to 3-methyl-1,2,4-oxadiazol-5-yl |
| XXI | 3-phenyl-5-(methoxymethyl)-2-(trifluoromethyl)thiophene |
| XXII | 3-phenyl-5-(methoxymethyl)-2-(trifluoromethyl)thiophene (regioisomer) |
| XXIII | 4-phenyl-5-(trifluoromethyl)thiophen-2-yl attached to 3-methyl-1,2,4-oxadiazol-5-yl |
| XXIV | 4-phenyl-5-(trifluoromethyl)thiophen-2-yl attached to 5-methyl-1,3,4-oxadiazol-2-yl |
| XXV | 4-phenyl-5-(trifluoromethyl)thiophen-2-yl attached to 5-methyl-1,2,4-oxadiazol-3-yl |
| XXXI | 3-(benzyloxy)phenyl methyl sulfide |

The compounds having formulas XX through XXV or XXXI also include all enantiomers thereof.

In cases where compounds of Formula IA are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Mon-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of Formula IA can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula IA to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula IA can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula IA in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit comprising an inhibitor compound of Formula IA and instructional material that describes administering the inhibitor compound or a composition comprising the inhibitor compound to a cell or a subject. This should be construed to include other embodiments of kits that are known to those skilled in the art, such as a kit comprising a (preferably sterile) solvent for dissolving or suspending the inhibitor compound or composition prior to administering the compound or composition to a cell or a subject. Preferably, the subject is a human.

The disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the disclosed compounds.

Processes for preparing compounds of Formula IA or for preparing intermediates useful for preparing compounds of Formula IA are provided as further embodiments. Intermediates useful for preparing compounds of Formula IA are also provided as further embodiments. The processes are provided as further embodiments and are illustrated in the schemes herein wherein the meanings of the generic radicals are as given above unless otherwise qualified.

Processes for preparing compounds of Formula IA or for preparing intermediates useful for preparing compounds of Formula IA are provided as further embodiments of the invention. Intermediates useful for preparing compounds of Formula IA are also provided as further embodiments of the invention. The compounds of the invention can be prepared using starting materials and methods known in the art.

The syntheses of compounds having formula IA are illustrated in FIGS. 1-12.

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

EXAMPLES

Materials and Methods

All non-aqueous reactions were carried out in oven or flame-dried glassware under an argon or nitrogen atmosphere with dry solvents and magnetic stirring, unless otherwise stated. The argon and nitrogen were dried by passing through a tube of Drierite. Anhydrous diethyl ether ($Et_2O$), toluene, dichloromethane ($CH_2Cl_2$), methanol (MeOH), and tetrahydrofuran (THF) were purchased from Aldrich or VMR Chemicals and used as received. THF was dried over activated molecular sieves (4 Å) prior to use. All other reagents were purchased from Acros chemicals and Aldrich chemicals.

Except as indicated otherwise, reactions were monitored by thin layer chromatography (TLC) using 0.25 mm Whatman precoated silica gel plates. Flash chromatography was performed with the indicated solvents and Dynamic Adsorbents silica gel (particle size 0.023-0.040 mm).

Proton ($^1H$) and carbon ($^{13}C$) NMR spectra were recorded on a Varian Unitylnova 500/51 or Varian Unitylnova 300/54 at 300K unless otherwise noted. Chemical shifts are reported in ppm (δ) values relative to the solvent as follows: $CDCl_3$ (δ 7.24 for proton and δ 77.0 for carbon NMR), DMSO-$d_6$ (δ 2.50 for proton and δ 39.5 for carbon NMR) $CD_3OD$ (δ 3.31 for proton and δ 47.6 for carbon NMR).

Other abbreviations: acetonitrile (MeCN), acetic acid (AcOH), chloroform ($CHCl_3$), ethyl acetate (EtOAc), isopropanol (i-PrOH), methanol (MeOH), trifluoroacetic acid (TFA), water ($H_2O$), hydrochloric acid (HCl), sodium sulfate ($Na_2SO_4$), sodium bicarbonate ($NaHCO_3$), potassium carbonate ($K_2CO_3$), phosphorus pentoxide ($P_2O_5$), lithium hydroxide (LiOH), aqueous (aq.), hour (h), minute (min), room temperature (r.t.).

General Experimental Procedures

General Procedure A: Schotten-Baumen Protection of Free Amino Acids

To a stirring solution of 10% sodium carbonate (weight to volume) in water (25 mL) was added the free amino acid (9.3 mmol). To this solution was added either di-tert-butyl dicarbonate or N-(Benzyloxycarbonyloxy)succinamide (18.6 mmol) followed by 1,4-dioxanes (18.6 mL). This solution was allowed to stir for approximately 15 hours at which point the reaction mixture was extracted with three 15 mL potions of diethyl ether. The aqueous layer was then acidified to a pH of 3 and immediately extracted with four to five 25 mL portions of ethyl acetate. The organic layers were then combined and washed with a 10 mL portion of brine, dried with $MgSO_4$, and evaporated to dryness. The crude material was immediately taken on with no further purification.

General Procedure B: Conversion of a Carboxylic Acid to a Primary Amide

To the stirring solution of the carboxylic acid (9.3 mmol) in 20 mL of DCM was added triethylamine (3.76 g). After cooling the solution to −25° C., iso-butylchloroformate (2.54 g) was added dropwise to the mixture. This mixture was stirred for approximately 45 minutes and analyzed by TLC. Upon completion of the reaction, 3.5 mL of a 28% solution of ammonium hydroxide in water was added to the reaction mixture (still at −25° C.) and stirred for an additional 30 minutes. After this time the mixture was warmed to r.t. and stirred for an additional 15 hours at this temperature. When the reaction was deemed complete by TLC, the reaction mixture was evaporated to an aqueous solution, diluted with 150 mL of EtOAc and extracted with four 15 mL potions of de-ionized water. The organic layer was washed once with brine, dried over $MgSO_4$ and evaporated to dryness. The crude mixture was taken on without further purification.

General Procedure C: Conversion of a Primary Amide to a Nitrile

The primary amide (9.3 mmol) and triethylamine (1.9 g) was taken up in 93 mL of anhydrous THF and cooled to 0° C. Upon cooling, trifluoroacetic anhydride (2.34 g) was added drop-wise to the reaction mixture; after 10 minutes of stirring at this low temperature the reaction mixture was allowed to warm to ambient temperature and evaporated to dryness. The crude organic mixture was taken up in 200 mL of EtOAc and extracted with four 15 mL portions of 1N HCl followed by one 10 mL portion of brine. The organic layer was then dried of $MgSO_4$ and evaporated to an oil. The crude product was purified by flash chromatography and identified by NMR analysis.

General Procedure D: Deprotection of N-Boc Protected Amino-Nitriles

To a stirring solution of the N-Boc protected amino-nitrile (1.2 mmol) in anhydrous DCM (12 mL) was added trifluoroacetic acid, drop-wise (12 mL) at room temperature. After 15 minutes the reaction mixture was evaporated to dryness. Three 5 mL portions of methanol were added to the crude oil and evaporated immediately; three 5 mL portions of diethyl ether were then added and evaporated in the same fashion to yield the trifluoroacetate salt as either a yellowish solid or oil, depending on the substrate. This salt was carried on immediately in the same reaction vessel.

General Procedure E: N-Cbz Deprotection of Amino-Nitriles

To a stirring solution of the N-Cbz protected (0.390 g, 1.4 mmol) amino-nitrile in bench-top EtOAc was added 0.039 g of Pd(OH)/C. The ambient atmosphere was thoroughly evacuated under vacuum and replace with an atmosphere of exclusively hydrogen gas. The reaction was monitored closely by TLC. When most of the starting material had been consumed, the hydrogen atmosphere was removed and the reaction mixture was filtered through celite 545. The filtrate was captured in a larger round bottom flask and stirred vigorously while HCl (2.1 mmol) was added as a 2.0 M solution in diethyl ether. The mixture was allowed to stir for 10 minutes at ambient temperature at which point it was evaporated to dryness. The HCl salt was tritrated with diethyl ether and collected as an off-white solid. No further purification was performed.

General Procedure F: PyBOP Mediated Couplings of HCl or TFA Salts to Acids

To a suspension of either the HCl or TFA salt of an amine (0.43 mmols) in anhydrous DCM (9 mL) was added the acid (0.43 mmols) and PyBOP (0.223 g). Finally, diisopropylethylamine (0.222 g) was added and the reaction was allowed to stir for 15 hours. At this time the reaction mixture was evaporated to dryness and reconstituted in 100 mLs of EtOAc. The solution was extracted with four 15 mL portions of 1N HCl followed by one portion of brine. The organic layer was dried with $MgSO_4$ and evaporated to dryness. The crude organic material was purified by flash chromatography.

General Procedure G: Suzuki Coupling of Para- and Meta-Bromobenzaldehyde to a Terminal Alkene To a 0.5 M solution of 9-BBN in THF was added 8.1 mmols of 1-octene. The mixture was allowed to stir for 15 hours at ambient temperature at which time it was diluted with 2.7 mL of a 3 M solution of sodium hydroxide. In a separate flask a bromobenzaldehyde (1 g, 5.4 mmols) was combined with a catalytic amount of tetrakis(triphenylphosphine)palladium under an anhydrous, nitrogen atmosphere. After stirring at r.t. for approximately 10 minutes, the solution containing the benzaldehyde was cannulated into the flask containing the terminal borane in THF. This mixture was then refluxed until the reaction was deemed complete by TLC. Water was then removed from the reaction mixture using a separatory funnel and the crude mixture was evaporated to dryness and purified by flash chromatography.

General Procedure H: Pinnick Oxidation of Aldehydes to Carboxylic Acids

An aryl aldehyde (3.05 mmol) was taken up in a 78 mL solution of 1:1 THF and tert-butyl alcohol followed by 1.71 g of 2-methyl-2-butene. In a separate flask 0.83 g of sodium chlorite and 1.26 g of sodium phosphate monobasic were dissolved in 13 mL of water. Once fully dissolved, the aqueous solution was poured into the stirring organic solution and stirred vigorously. Upon completion by TLC, the reaction mixture was evaporated to dryness and reconstituted in 100 mLs of EtOAc. The organic solution was extracted with three 15 mL portions of 1N HCl followed by a single 10 mL portion of brine. The organic layer was finally dried over magnesium sulfate and evaporated to dryness. No further purification was necessary.

General Procedure I: Formation of N-Boc Protected Amidines

A nitrile (0.25 mmols) was dissolved in 0.7 mL of anhydrous methanol. To this solution was added 0.125 mmols of sodium methoxide as a 0.5 M solution of sodium methoxide in methanol. This solution was stirred at ambient temperature for 15 hours. When the initial intermediate appeared in a modest abundance by TLC, 0.073 g of ammonium bromide was added directly to the reaction mixture. After approximately one hour the intermediate was consumed and the reaction mixture was evaporated to dryness. After co-evaporation with diethyl ether, the crude mixture was dried under high vacuum for 2 hours. After this time, the mixture was taken up in 2.5 mL of anhydrous THF and 0.207 g of potassium carbonate was added to the reaction and stirred for 45 minutes. Finally, 0.177 g of di-tert-butyl dicarbonate was added and the reaction was allowed to proceed for an additional 15 hours. At this time, the reaction was evaporated to dryness and immediately subjected to flash chromatography.

General Procedure J: Deprotection of N-Boc Protected Amidines

An N-Boc protected amidine (0.11 mmols) was dissolved in 1.1 mL of anhydrous DCM; to this mixture was added 1.1 mL of trifluoroacetic acid. The reaction was monitored by TLC. When the reaction appeared to be completed (usually after 30 minutes) the reaction mixture was evaporated to dryness. Three portions of methanol (approx. 2 mL) were added and immediately evaporated; the same procedure was then carried out with diethyl ether. The crude oily material was then dried under high vacuum for several minutes before being taken up in 2.0 M hydrogen chloride in diethyl ether.

This mixture was stirred for approximately 1 hour before evaporation to dryness. The product was usually recovered as an off-white or yellow solid after trituration with diethyl ether. No further purification was performed.

General Procedure K: Direct Conversion of Nitriles to Amidines

A nitrile (0.21 mmols) was taken up in 0.6 mL of anhydrous methanol and 42 μL of a solution of 0.5 M sodium methoxide in methanol was immediately added. This mixture was allowed to stir for 15 hours at which time 0.022 mg of ammonium bromide was added to the reaction. When the reaction appeared complete by TLC, the reaction mixture was evaporated to dryness and the crude material was taken up in a 1:1 mixture of ethyl acetate and hexanes. After approximately 45 minutes of stirring the product was filtered out as a white solid. No further purification was performed.

Example 1

4-octylbenzaldehyde (1)

General procedure G was used to convert 5.4 mmols of p-bromobenzaldehyde to 4-octyl benzaldehyde to produce 1.15 g of the desired product after purification by column chromatography. Spectral data was consistent with previously reported compounds.

Example 2

4-octylbenzoic acid (2)

General procedure H was used to convert 5.4 mmols (1.15 g) of 1 to the title product. 1.3 g of product was recovered and carried on. Spectral data was consistent with previously reported compounds.

Example 3

(S)-tert-butyl 1-amino-1-oxopropan-2-ylcarbamate (3)

General procedure A and general procedure B were used to convert 1 g of alanine into 2.11 g of the title product. No further purification was conducted other than that described in the general procedure; spectral data was consistent with previously reported compounds.

Example 4

(S)-tert-butyl 1-cyanoethylcarbamate (4)

General procedure C was used to convert 1.082 g (5.7 mmols) of 3 to the title product. The product was purified with flash chromatography using a solvent system of ethyl acetate and hexanes (1:3, $R_f$=0.42) to yield 0.528 g (3.1 mmols) of the desired product. $^1$H NMR (500 MHz, CDCl$_3$) δ 4.82 (s, 1H), 4.62 (s, 1H), 1.54 (d, J=7.2, 3H), 1.46 (s, 8H). $^{13}$C NMR (126 MHz, CDCl$_3$) δ 154.10, 119.53, 37.57, 28.21, 19.62.

Example 5

(S)—N-(1-cyanoethyl)-4-octylbenzamide (5)/VPC94073

General procedure D was used to deprotect 2.8 mmols of 4 and immediately couple to 2.8 mmols of 2 using general procedure F. The product was purified using column chromatography using a solvent system of ethyl acetate and hexanes (1:3, $R_f$=0.5) to yield 0.340 g (1.2 mmols) of the desired product. $^1$H NMR (300 MHz, CDCl$_3$) δ 7.71 (d, J=8.2, 2H), 7.23 (d, J=7.6, 2H), 6.75 (s, 1H), 5.27-5.06 (m, 1H), 2.71-2.55 (m, 2H), 1.64 (d, J=7.2, 2H), 1.61-1.53 (m, 1H), 1.35-1.13 (m, 10H), 0.87 (t, J=6.8, 3H). $^{13}$C NMR (126 MHz, CDCl$_3$) δ 166.56, 147.99, 129.93, 128.81, 128.62, 127.18, 127.03, 119.40, 52.73, 48.54, 36.23, 35.86, 31.84, 31.22, 31.15, 29.41, 29.22, 22.64, 19.60, 18.71, 14.11.

Example 6

VPC94075

General procedure K was used to convert 0.35 mmol (0.1 g) of 5 into the title product. No purification techniques were employed beyond that described in the general procedure. 32.1 mgs were submitted for biological evaluation. $^1$H NMR (500 MHz, DMSO) δ 9.09 (s, 3H), 8.95 (s, 1H), 7.91 (d, J=8.2, 2H), 7.27 (d, J=8.3, 2H), 4.70 (d, J=6.9, 1H), 2.60 (t, J=7.6, 2H), 1.55 (s, 2H), 1.50 (d, J=7.2, 3H), 1.32-1.12 (m, 10H), 0.83 (t, J=7.0, 3H). $^{13}$C NMR (126 MHz, DMSO) δ 172.91, 166.97, 146.97, 130.97, 128.52, 128.36, 47.59, 35.41, 31.71, 31.18, 29.24, 29.11, 29.04, 22.53, 18.83, 14.40.

Example 7

4-decylbenzaldehyde (6)

General procedure G was used to couple 1-decene (8.1 mmol) to 4-bromobenzaldehyde (5.4 mmol) to yield 1.25 g (5.1 mmol) of the title product after column chromatography. Spectral data was consistent with previously reported compounds.

Example 8

4-decylbenzoic acid (7)

General procedure H was used to convert 5.1 mmols of 6 to 5.1 mmols of the title product. No purification was performed beyond the general procedure; spectral data was consistent with previously reported compounds.

Example 9

(S)—N-(1-cyanoethyl)-4-decylbenzamide (8)

General procedure D was used to deprotect 0.198 g (1.2 mmols) of 4. The product was immediately carried on using general procedure F and coupled to 1.2 mmols of 7. The title product was purified with flash chromatography using a solvent system of ethyl acetate and hexanes (1:3) to yield 0.2 g (0.63 mmols). $^1$H NMR (500 MHz, CDCl$_3$) δ 7.23 (d, J=8.2, 2H), 6.94 (d, J=7.3, 1H), 5.19-5.11 (m, 1H), 2.66-2.60 (m, 2H), 1.64 (dd, J=2.0, 7.2, 2H), 1.59 (dd, J=5.9, 13.3, 2H), 1.30 (dd, J=18.9, 22.5, 13H), 0.88 (t, J=6.9, 3H). $^{13}$C NMR (126 MHz, CDCl$_3$) δ 173.67, 166.98, 147.92, 147.35, 129.98, 128.73, 127.28, 119.51, 52.38, 48.45, 36.25, 35.86, 31.88, 31.16, 29.59, 29.56, 29.45, 29.31, 29.23, 22.67, 19.47, 18.62, 14.12.

Example 10

VPC94273

General procedure K was performed to convert 0.21 mmols of 8 to the title product. No further purification was carried our other than that described in the general procedure.

Example 11

4-hexylbenzaldehyde (9)

General procedure G was used to couple 8.1 mmols of 1-hexene to 5.4 mmols of 4-bromobenzaldehyde. 5.1 mmols of the title product was recovered after purification by flash chromatography. Spectral data was consistent with previously described compounds.

Example 12

4-hexylbenzoic acid (10)

General procedure H was used to convert 5.1 mmols of 9 to the title product. After extraction 5.1 mmols of the title product was recovered, no further purification was necessary. Spectral data was consistent with previously described compounds.

Example 13

(S)—N-(1-cyanoethyl)-4-hexylbenzamide (11)

General procedure D was used to deprotect 0.210 g (1.23 mmols) of 4. The product was immediately carried on using general procedure F and coupled to 1.23 mmols of 10. The title product was purified with flash chromatography using a solvent system of ethyl acetate and hexanes (1:3) to yield 0.106 g (0.41 mmols). $^1$H NMR (500 MHz, CDCl$_3$) δ 7.74-7.68 (m, 2H), 7.25 (d, J=8.2, 2H), 6.61 (s, 1H), 5.20-5.11 (m, 1H), 2.70-2.61 (m, 2H), 1.66 (t, J=6.6, 3H), 1.60 (dd, J=7.3, 14.9, 2H), 1.37-1.22 (m, 6H), 0.88 (t, J=6.8, 3H). $^{13}$C NMR (126 MHz, CDCl$_3$) δ 173.95, 166.58, 148.00, 148.00, 131.31, 129.95, 128.78, 128.62, 127.20, 127.03, 119.42, 77.27, 77.02, 76.76, 52.57, 48.42, 36.24, 35.85, 31.63, 31.10, 28.87, 22.56, 19.57, 18.68, 14.07.

Example 14

VPC94253

General procedure K was used to convert 0.27 mmols of 11 to the title product. No further purification was carried our other than that described in the general procedure. $^1$H NMR (500 MHz, DMSO) δ 8.71 (d, J=5.3, 1H), 7.89 (d, J=8.0, 2H), 7.30 (d, J=7.8, 2H), 4.63 (dd, J=6.3, 12.3, 1H), 2.71-2.57 (m, 2H), 1.56 (s, 2H), 1.50 (d, J=7.2, 2H), 1.26 (s, 7H), 0.84 (s, 3H).

Example 15

N-(cyanomethyl)-4-octylbenzamide (12)

General procedure F was used to couple 0.1 g (0.42 mmols) of 2 and 0.065 g of amino acetonitrile. The title product was purified with flash chromatography using a solvent system of ethyl acetate and hexanes (2:3) to yield 0.104 g (0.38 mmols). $^1$H NMR (300 MHz, CDCl$_3$) δ 7.70 (d, J=8.3, 2H), 7.25 (d, J=7.6, 2H), 6.78 (t, J=5.5, 1H), 4.37 (d, J=5.8, 2H), 2.81-2.51 (m, 2H), 1.62 (dt, J=7.4, 22.1, 3H), 1.26 (s, 10H), 0.87 (t, J=6.7, 3H). $^{13}$C NMR (75 MHz, CDCl$_3$) δ 167.32, 148.82, 130.03, 129.08, 127.46, 117.30, 77.67, 77.25, 76.83, 36.09, 32.06, 31.35, 29.62, 29.44, 28.19, 22.86, 14.31.

Example 16

VPC94131

General procedure K was used to convert 0.104 g (0.38 mmols) of 12 into the title product. No purification other than that described in the general procedure was used and 0.06 g (0.16 mmols) of product was recovered. $^1$H NMR (500 MHz, DMSO) δ 8.94 (s, 1H), 7.82 (d, J=8.0, 4H), 7.29 (d, J=7.9, 2H), 4.15 (d, J=5.2, 2H), 2.61 (t, J=7.4, 2H), 1.68-1.47 (m, 2H), 1.23 (d, J=16.7, 9H), 0.83 (t, J=6.4, 3H). $^{13}$C NMR (126 MHz, DMSO) δ 168.79, 167.52, 147.03, 130.99, 128.61, 128.17, 35.39, 31.70, 31.17, 29.23, 29.10, 29.02, 22.51, 14.40.

Example 17

N-(cyanomethyl)decanamide (13)

General procedure F was used to couple 0.1 g (0.58 mmols) of decanoic acid and 0.065 g of amino acetonitrile. The title product was purified with flash chromatography using a solvent system of ethyl acetate and hexanes (2:3) to yield 0.104 g (0.38 mmols). $^1$H NMR (500 MHz, CDCl$_3$) δ 6.09 (s, 1H), 4.18 (d, J=5.8, 2H), 2.35-2.14 (m, 2H), 1.78-1.55 (m, 2H), 1.27 (d, J=17.2, 12H), 0.87 (t, J=6.9, 3H). $^{13}$C NMR (126 MHz, CDCl$_3$) δ 173.15, 116.12, 77.26, 77.01, 76.76, 36.06, 31.82, 29.38, 29.27, 29.23, 29.16, 27.34, 25.28, 22.63, 14.09.

Example 18

(S)-methyl 2-(4-octylbenzamido)propanoate (14)

General procedure F was used to couple 0.31 mmols of H-D-Ala-OMe.HCl to 0.31 mmols of 2. The product was isolated by flash chromatography to yield 0.075 g (0.23 mmols). $^1$H NMR (300 MHz, CDCl$_3$) δ 7.75 (d, J=8.1, 2H), 7.27 (d, J=8.1, 2H), 6.77 (s, 1H), 4.84 (s, 1H), 3.82 (s, 3H), 2.79-2.60 (m, 2H), 1.64 (s, 2H), 1.55 (d, J=7.1, 3H), 1.29 (s, 14H), 0.90 (t, J=6.9, 3H).

Example 19

VPC94177

The intermediate 14 (0.23 mmols, 0.075 g) was dissolved in 4.6 mL of 2-propanol. In a separate flask, sodium hydroxide (0.46 mmols, 0.0184 g) was dissolved in 1.5 mL of water. The sodium hydroxide solution was immediately added to the stirring solution of 14 and the mixture was heated to 60° C. When hydrolysis was complete by TLC, the mixture was cooled to ambient temperature and evaporated to dryness. The mixture was next reconstituted in a suspension of ethyl acetate and aqueous 1N HCl (4:1) and the aqueous layer was extracted with 3 additional portions of ethyl acetate. The organic layers were then combined and washed with a final portion of brine and dried with magnesium sulfate. The title product was purified by flash chromatography and 69 mgs of the title product was recovered; 10.1 mgs was submitted for biological evaluation. $^1$H NMR (300 MHz, CDCl$_3$) δ 7.71 (d, J=8.2, 2H), 7.31-7.16 (m, 3H), 6.80 (d, J=6.9, 1H), 4.79 (t, J=7.1, 1H), 2.76-2.51 (m, 2H), 1.57 (d, J=7.1, 5H), 1.27 (d, J=7.3, 11H), 0.87 (t, J=6.7, 3H). $^{13}$C NMR (75 MHz, CDCl3)

δ 176.41, 168.48, 147.81, 131.10, 129.06, 127.39, 48.95, 36.08, 32.07, 30.81, 29.24, 23.00, 18.37, 14.32.

Example 20

VPC94181

The intermediate 14 (0.437 g, 1.36 mmols) was dissolved in a mixture of 10 mL of anhydrous ethanol and 5 mL of anhydrous THF. To this mixture was added anhydrous calcium chloride (0.53 g, 4.08 mmols) and the mixture was immediately cooled to 0° C. Sodium borohydride was added slowly was a solid and the reaction was allowed to warm slowly to ambient temperature. When the reaction appeared complete by TLC, reaction mixture was cooled back to 0° C. and 1 N HCl was added until the reaction mixture to become more homogeneous. This mixture was then diluted with a large excess of ethyl acetate (approximately 100 mL). This layer was recovered and the aqueous layer was extracted with 3 additional 20 mL portions of ethyl acetate. The organic layers were combined and washed with one portion of brine and dried with magnesium sulfate. The title product was recovered with column chromatography in a nearly quantitative yield (1.35 mmols, 0.390 g). $^1$H NMR (500 MHz, CDCl$_3$) δ 7.68 (d, J=8.1, 1H), 7.21 (d, J=8.1, 1H), 6.39 (s, 1H), 4.27 (s, 1H), 3.76 (dd, J=3.5, 11.0, 1H), 3.63 (dd, J=5.7, 11.0, 1H), 2.73-2.53 (m, 2H), 1.68-1.50 (m, 1H), 1.37-1.17 (m, 7H), 0.87 (t, J=6.9, 1H). $^{13}$C NMR (75 MHz, CDCl$_3$) δ 168.38, 147.21, 131.80, 128.75, 127.24, 77.69, 77.26, 76.84, 67.01, 48.28, 36.02, 32.07, 31.44, 29.64, 29.46, 22.87, 17.34, 14.32.

Example 21

VPC94193

General procedure F was used to couple L-alaninamide-.HCl (0.43 mmols, 0.054 g) to 2 (0.43 mmols, 0.1 g). Standard procedure and work up were employed to isolate 0.065 g (0.215 mmols) of the title product after recrystallization with ethyl acetate and hexanes. $^1$H NMR (500 MHz, CD$_3$OD) δ 7.86-7.69 (m, 2H), 7.28 (d, J=8.2, 2H), 4.56 (q, J=7.2, 1H), 2.78-2.55 (m, 2H), 1.63 (s, 2H), 1.47 (d, J=7.2, 3H), 1.37-1.19 (m, 10H), 0.89 (t, J=7.0, 3H). $^{13}$C NMR (126 MHz, CD$_3$OD) δ 176.59, 168.54, 147.05, 131.15, 128.13, 127.16, 35.32, 31.59, 28.97, 22.29, 16.88, 13.00.

Example 22

VPC94199

General procedure F was used to couple 2 (0.43 mmols, 0.1 g) to isopropyl amine (0.43 mmols, 0.025 g). The general procedure and work up were employed to yield 0.095 g (0.344 mmols) of the title product after column chromatography. $^1$H NMR (500 MHz, CDCl$_3$) δ 7.66 (d, J=8.1, 2H), 7.22 (d, J=8.0, 2H), 5.92 (d, J=6.9, 1H), 4.36-4.21 (m, 1H), 2.73-2.55 (m, 2H), 1.65-1.52 (m, 2H), 1.37-1.19 (m, 16H), 0.87 (t, J=6.9, 3H). $^{13}$C NMR (126 MHz, CDCl$_3$) δ 166.67, 146.62, 132.28, 128.52, 126.77, 41.77, 35.78, 31.84, 31.25, 29.42, 29.22, 29.21, 22.89, 22.64, 14.10.

Example 23

(S)-4-octyl-N-(1-oxopropan-2-yl)benzamide (15)

To a flame dried flask was added oxalyl chloride (1.5 mmols, 0.19 g) which was immediately cooled to −78° C. DMSO (1.5 mmols, 0.177 g) was then added as a solution in DCM (3 mL) to the oxalyl chloride and allowed to stir for 15 minutes at this low temperature. VPC94181 (1 mmol, 0.29 g) was then added dropwise as a solution in 5 mL of DCM. The mixture was allowed to stir for an additional 30 minutes at which time triethylamine (3 mmols, 0.303 g) was added. The reaction mixture was then allowed to warm slowly to room temperature at which time it was poured onto a saturated solution of ammonium chloride in water. The aqueous layer was extracted with 3 additional portions of DCM. The organic layers were combined, washed with one potion of brine and dried with magnesium sulfate. After flash chromatography 0.5 mmols of the title product were recovered. $^1$H NMR (300 MHz, CDCl$_3$) δ 9.64 (s, 1H), 7.73 (d, J=8.2, 2H), 7.25 (d, J=8.4, 2H), 6.83 (s, 1H), 4.88-4.58 (m, 1H), 2.79-2.51 (m, 2H), 1.61 (s, 3H), 1.48 (d, J=7.4, 3H), 1.27 (d, J=7.4, 10H), 0.87 (t, J=6.7, 3H).

Example 24

VPC94201

To a stirring solution of 15 (0.17 mmols, 0.052 g) in anhydrous methanol (3 mL) was added 4 Å molecular sieves. Ammonium acetate (0.17 mmols, 0.013 g) and sodium cyanoborohydride (0.17 mmols, 0.011 g) were then added and the solution was allowed to stir for 15 hours. At this time, the reaction mixture was filtered through a medium fritted funnel and evaporated to dryness. The dried material was taken up in a 10% aqueous sodium hydroxide solution and extracted with 3 portions of ethyl acetate. The organic layers were combined, washed with brine, dried with magnesium sulfate and evaporated to dryness. The crude material when finally suspended in anhydrous diethyl ether and a small drop of 12N HCl was used to precipitate the title product as a white solid, purified by trituration. $^1$H NMR (500 MHz, CD$_3$OD) δ 8.38 (d, J=7.1, 1H), 7.68 (d, J=7.9, 2H), 7.18 (d, J=7.8, 2H), 4.41 (s, 1H), 3.21 (s, 1H), 2.65 (t, J=7.6, 2H), 1.62 (s, 2H), 1.33 (dd, J=16.8, 37.6, 14H), 0.87 (d, J=6.9, 3H). $^{13}$C NMR (126 MHz, CD$_3$OD) δ 169.78, 147.30, 130.66, 128.12, 127.49, 90.56, 53.23, 43.43, 35.52, 31.66, 31.12, 29.23, 29.01, 22.38, 17.12, 13.29, 12.94, 10.03.

Example 25

(S)—N-(1-cyanoethyl)decanamide (16)

General procedure D was used to deprotect 0.160 g (0.94 mmols) of 4. The product was immediately carried on using general procedure F and coupled to decanoic acid (0.94 mmol, 0.162 g). The product was purified via flash chromatography to yield 0.115 g (0.51 mmols) of the title product. $^1$H NMR (300 MHz, CDCl$_3$) δ 6.07 (s, 1H), 4.94 (dq, J=7.2, 14.5, 1H), 2.26-2.16 (m, 2H), 1.69-1.58 (m, 2H), 1.54 (d, J=7.2, 3H), 1.26 (d, J=6.4, 12H), 0.86 (t, J=6.7, 3H).

Example 26

VPC94247

General procedure K was used to convert 17 (0.34 mmols, 0.077 g) to the title product. After purification methods described in the general procedure, the compound was submitted for biological evaluation. $^1$H NMR (500 MHz, DMSO) δ 8.28 (s, 1H), 7.47 (bs, 4H), 4.43-4.26 (m, 1H), 2.14 (t, J=7.4, 2H), 1.46 (s, 2H), 1.33 (d, J=7.2, 3H), 1.21 (s, 12H), 0.83 (t, J=6.7, 3H). ¹³C NMR (126 MHz, DMSO) δ 173.52, 172.78, 46.98, 35.16, 31.72, 29.14, 25.13, 22.54, 18.57, 14.42.

Example 27

1-tert-butyl 2-methyl pyrrolidine-1,2-dicarboxylate (17)

D,L-proline (8.7 mmols, 1 g) was dissolved in methanol (75 mL) and cooled to 0° C. Thionyl chloride (17.4 mmols, 2.07 g) was then added dropwise to the solution. The reaction mixture was then allowed to warm slowly to room temperature and stirred for 15 hours. At this time the reaction mixture was evaporated to dryness. Three 15 mL portions of methanol were added and evaporated immediately followed by one 15 mL portion of diethyl ether. The intermediate was collected as a white crystalline solid. After drying under high vacuum for a few hours, the white solid was suspended in DCM (87 mL) and triethylamine (34.8 mmols, 3.52 g) was added followed by di-tert-butyl dicarbonate (9.57 mmol, 1.13 g). The reaction was monitored by TLC and when complete, the reaction mixture was evaporated to dryness. The crude material was then taken up in ethyl acetate and washed with three 15 mL portions of aqueous 1N HCl followed by one 10 mL portion of brine. The organic layer was then dried with magnesium sulfate and evaporated to dryness. No further purification was carried out; 1.556 g (6.8 mmol) was recovered after two steps. ¹H NMR (500 MHz, CDCl₃) δ 4.31 (d, J=8.6, 1H), 4.20 (dd, J=4.2, 8.5, 1H), 3.77-3.69 (m, 3H), 3.58-3.50 (m, 1H), 3.45 (dd, J=6.8, 10.6, 1H), 3.37 (s, 1H), 2.27-2.14 (m, 1H), 2.02-1.90 (m, 2H), 1.90-1.81 (m, 1H), 1.46 (d, J=12.5, 4H), 1.43-1.36 (m, 6H). ¹³C NMR (126 MHz, CDCl₃) δ 173.37, 153.80, 79.84, 59.09, 58.69, 52.09, 51.92, 46.53, 46.29, 30.85, 29.90, 28.40, 28.27, 24.32, 23.67, 18.38.

Example 28 tert-butyl 2-carbamoylpyrrolidine-1-carboxylate (18)

To a solution of 18 (6.8 mmol, 1.556 g) in methanol (113 mLs) was added a solution of 28% ammonium hydroxide (aqueous, 76 mL). The solution was vigorously stirred for 3 days after which time it was evaporated to a crude oil and purified by flash chromatography; 2.9 mmols (0.626 g) of the title product was recovered. ¹H NMR (300 MHz, CD₃OD) δ 4.16 (s, 1H), 3.42 (s, 1H), 2.36-2.07 (m, 1H), 1.91 (s, 3H), 1.45 (d, J=7.3, 9H).

Example 29 tert-butyl 2-cyanopyrrolidine-1-carboxylate (19)

General procedure C was used to convert 18 (2.9 mmol, 0.626 g) to the title product. After general work up procedures and flash chromatography, 0.24 g (1.2 mmol) of the title product was recovered. ¹H NMR (500 MHz, CDCl₃) δ 4.56 (s, 0.5H), 4.45 (s, 0.5H), 3.52 (s, 1H), 3.37 (d, J=8.4, 1H), 2.24 (s, 2H), 2.17-1.98 (m, 2H), 1.49 (d, J=16.4, 9H). ¹³C NMR (126 MHz, CDCl₃) δ 156.99, 119.14, 81.58, 47.17, 45.70, 31.52, 28.29, 23.79.

Example 30

1-(4-octylbenzoyl)pyrrolidine-2-carbonitrile (20)

General procedure D was used to deprotect 19 (1.2 mmol, 0.24 g). The product was immediately carried on and coupled to 2 (1.2 mmol, 0.281 g) using general procedure F. After standard work up procedures the title product was recovered from flash chromatography to yield 0.238 g (0.76 mmol) after two steps. ¹H NMR (500 MHz, CDCl₃) δ 7.50 (d, J=8.1, 2H), 7.21 (dd, J=7.9, 14.6, 2H), 4.91 (s, 0.5H), 4.66 (s, 0.5H), 3.67 (s, 1H), 3.56 (s, 1H), 2.66-2.60 (m, 2H), 2.32 (s, 1H), 2.17 (s, 1H), 2.01 (s, 1H), 1.88 (s, OH), 1.60 (d, J=7.5, 2H), 1.28 (dd, J=7.5, 14.4, 10H), 0.87 (t, J=6.8, 3H). ¹³C NMR (126 MHz, CDCl₃) δ 173.09, 146.33, 133.26, 132.60, 128.43, 128.21, 127.64, 127.44, 118.72, 59.24, 52.28, 50.05, 46.85, 35.84, 31.85, 31.19, 29.41, 29.22, 25.42, 22.64, 14.11.

Example 31

VPC94281

General procedure K was used to convert 20 (0.44 mmol, 0.136 g) to the title product. After general purification techniques the product was recovered as a white solid. ¹H NMR (500 MHz, DMSO) δ 9.06 (s, 1H), 7.62 (d, J=8.0, 2H), 7.26 (d, J=8.0, 2H), 4.62 (s, 0.5H), 3.83 (s, 0.5H), 3.43 (s, 1H), 2.59 (t, J=7.6, 2H), 2.36 (s, 1H), 1.92 (s, 1H), 1.83 (s, 2H), 1.56 (s, 2H), 1.24 (d, J=21.2, 10H), 0.83 (t, J=6.8, 3H). ¹³C NMR (126 MHz, DMSO) δ 171.43, 169.98, 145.62, 133.17, 128.40, 58.55, 50.69, 40.45, 40.28, 40.11, 39.94, 39.78, 39.61, 39.44, 35.42, 31.71, 31.41, 31.18, 29.24, 29.08, 25.69, 22.53, 14.42.

Example 32

(S)-tert-butyl 2-cyanopyrrolidine-1-carboxylate (21)

General procedure A was used to N-Boc protect 1 g (8.7 mmol) of L-proline. Standard work up procedures were employed. General procedure B was performed immediately with no further purification of the intermediate followed by general procedure C to yield 0.682 g (3.48 mmol) the title product after column chromatography. ¹H and ¹³C NMR spectra are identical to that reported for 19.

Example 33

(S)-1-(4-octylbenzoyl)pyrrolidine-2-carbonitrile (22)

General procedure D was used to deprotect 1 mmol of 21 and was immediately coupled to 2 using general procedure F. After column chromatography 0.23 g (0.73 mmol) of the title product was recovered. ¹H and ¹³C NMR spectra were identical to that reported for 20.

Example 34

(S)-tert-butyl amino(1-(4-octylbenzoyl)pyrrolidin-2-yl)methylenecarbamate (23)

General procedure I was used to form the title product from 0.73 mmol of 22. After formation of the amidine intermediate, an aqueous wash was performed. Other than this exception, all other work up and purification techniques were the same. 0.05 mmol of product were recovered. ¹H NMR (500 MHz, CDCl3) δ 7.49 (d, J=6.9, 2H), 7.23 (s, 2H), 4.91 (s, 1H), 3.62 (s, 2H), 2.63 (t, J=7.4, 2H), 2.48 (s, 1H), 2.22 (s, 1H), 2.00 (s, 1H), 1.82 (s, 1H), 1.61 (s, 2H), 1.50 (d, J=9.9, 8H), 1.28 (d, J=19.3, 12H), 0.88 (t, J=7.0, 3H). ¹³C NMR (126 MHz, CDCl3) δ 172.17, 146.05, 132.91, 128.39, 127.56, 127.35, 126.93, 126.83, 60.98, 60.33, 51.07, 50.51, 35.83, 31.86, 31.23, 29.43, 29.23, 28.18, 27.99, 26.92, 26.39, 25.46, 25.27, 22.66, 14.11.

Example 35

VPC95127

To a stirring solution of 2.0 M HCl in diethyl ether (0.6 mL) was added 23 (0.06 mmol, 0.025 g). This mixture was stirred at room temperature for 15 hours at which time it was evaporated to dryness. The resulting white solid was triturated with diethyl ether and toluene. 2.7 mgs were submitted for biological evaluation. $^1$H NMR (500 MHz, CD$_3$OD) δ 7.62 (d, J=5.6, 2H), 7.31 (d, J=7.8, 2H), 4.71 (dd, J=4.4, 6.9, 2H), 3.85 (s, 1H), 3.68 (s, 1H), 2.67 (t, J=7.8, 2H), 2.54 (d, J=9.1, 1H), 2.03 (d, J=24.3, 2H), 1.62 (d, J=13.3, 1H), 1.30 (d, J=22.8, 10H), 0.89 (t, J=6.7, 3H).

Example 36

4-phenoxybenzaldehyde (24)

To a stirring solution of p-fluorobenzaldehyde (1.6 mmol, 0.2 g) in dimethylformamide (8 mL) was added phenol (3.52 mmol, 0.33 g) and cesium carbonate (3.52 mmol, 1.15 g). The reaction mixture was headed to 90° C. for 3 hours at which time the reaction mixture was cooled to room temperature and filtered through a medium fritted funnel. The reaction mixture was then diluted with 125 mL of ethyl acetate and extracted with eight 15 mL portions of water followed by one 10 mL portion of brine. The organic layer was then dried with magnesium sulfate and evaporated to dryness. The title product was purified by column chromatography and 0.237 g (1.2 mmol) was recovered. $^1$H NMR (300 MHz, CDCl$_3$) δ 9.91 (s, 1H), 8.02 (s, OH), 7.92-7.79 (m, 2H), 7.49-7.37 (m, 2H), 7.23 (t, J=8.0, 2H), 7.14-7.01 (m, 4H), 6.89 (t, J=8.3, 2H). $^{13}$C NMR (75 MHz, CDCl$_3$) δ 191.28, 163.56, 156.41, 155.26, 132.28, 131.38, 130.41, 129.79, 125.23, 120.69, 120.45, 117.79, 115.61.

Example 37

4-phenoxybenzoic acid (25)

General procedure H was used to convert 1.2 mmols of 24 to the title product in quantitative yield. No purification beyond that described in the general procedure was used. Spectral data was consistent with previously reported compounds.

Example 38

(S)—N-(1-cyanoethyl)-4-phenoxybenzamide (26)

General procedure D was used to deprotect 1.2 mmols of 4 and immediately coupled to 1.2 mmols of 25 using general procedure F. The title product was purified by flash chromatography with ethyl acetate and hexanes to yield 0.53 mmol (0.14 g). $^1$H NMR (300 MHz, CDCl$_3$) δ 7.87-7.65 (m, 3H), 7.39 (t, J=7.8, 2H), 7.20 (d, J=6.7, 1H), 7.10-6.90 (m, 5H), 6.76 (s, 2H), 5.26-5.03 (m, 1H), 1.65 (d, J=7.2, 3H).

Example 39

VPC95051

General procedure K was used to convert 0.53 mmol (0.14 g) of 26 to the title product. After purification by standard trituration techniques, 29.8 mgs were submitted for biological evaluation. $^1$H NMR (500 MHz, DMSO) δ 7.99 (d, J=8.3, 4H), 7.87 (s, 5H), 7.19 (s, 1H), 7.04 (s, 4H), 4.61 (s, 1H), 1.48 (d, J=6.9, 3H). $^{13}$C NMR (126 MHz, DMSO) δ 172.83, 166.54, 160.35, 155.96, 130.74, 128.13, 124.83, 119.93, 117.69, 47.93, 18.70.

Example 40

4-(3-methoxyphenoxy)benzaldehyde (27)

To a solution of p-fluorobenzaldehyde (1.6 mmol, 0.2 g) in dimethylformamide (8 mLs) was added 3-methoxyphenol (3.52 mmol, 0.437 g) and cesium carbonate (3.52 mmol, 1.15 g). The reaction was heated to 90° C. for 3 hours at which time it was cooled to room temperature and filtered through a fritted funnel. The reaction mixture was diluted with 125 mL of ethyl acetate and extracted with eight 15 mL portions of water and one 10 mL portion of brine. The organic layer was dried with magnesium sulfate and evaporated to dryness. The crude oil was purified by flash chromatography to recover 0.365 g (1.6 mmol) of the title product. $^1$H NMR (300 MHz, CDCl$_3$) δ 9.92 (s, 1H), 7.84 (d, J=8.7, 2H), 7.29 (dd, J=5.7, 13.9, 1H), 7.07 (d, J=8.7, 2H), 6.76 (d, J=8.3, 1H), 6.72-6.57 (m, 2H), 3.80 (s, 3H). $^{13}$C NMR (75 MHz, CDCl$_3$) δ 190.99, 163.25, 161.38, 156.42, 132.15, 130.76, 117.91, 112.63, 110.81, 106.59, 55.66.

Example 41

4-(3-methoxyphenoxy)benzoic acid (28)

General procedure H was used to convert 1.6 mmols of 27 to the title product in quantitative yield. No further purification was carried out other than that described in the general procedure. $^1$H NMR (500 MHz, CDCl$_3$) δ 8.17-8.04 (m, 3H), 7.29 (dd, J=8.5, 16.6, 2H), 7.09-7.00 (m, 2H), 6.79-6.73 (m, 1H), 6.71-6.59 (m, 2H), 3.80 (s, 3H). $^{13}$C NMR (126 MHz, CDCl$_3$) δ 170.81, 162.46, 161.15, 156.38, 132.58, 130.70, 123.58, 117.47, 112.33, 110.41, 105.98, 55.29.

Example 42

(S)—N-(1-cyanoethyl)-4-(3-methoxyphenoxy)benzamide (29)

General procedure D was used to deprotect 0.62 mmols of 4 and immediately coupled to 0.62 mmols of 28 using general procedure F. After flash chromatography, 0.29 mmols (0.087 g) of the title product was recovered. $^1$H NMR (500 MHz, CDCl$_3$) δ 7.77 (d, J=8.9, 2H), 7.27 (dd, J=6.7, 9.6, 1H), 7.00 (d, J=8.9, 2H), 6.83 (d, J=8.0, 1H), 6.73 (dd, J=2.4, 8.3, 1H), 6.64-6.55 (m, 2H), 5.13 (dq, J=7.2, 14.5, 1H), 3.78 (s, 3H), 1.65 (d, J=7.2, 3H). $^{13}$C NMR (126 MHz, CDCl$_3$) δ 166.03, 161.07, 156.72, 130.44, 129.26, 128.99, 126.89, 119.48, 117.83, 111.97, 110.17, 105.93, 77.29, 77.04, 76.78, 55.41, 36.33, 19.46, 18.59.

Example 43

VPC95075

General procedure K was used to convert 0.29 mmol of 29 to the title product. Standard purification techniques were employed; 47.1 mgs were submitted for biological evaluation. $^1$H NMR (500 MHz, DMSO) δ 8.73 (s, 1H), 8.55-8.09 (m, 3H), 7.99 (d, J=8.9, 2H), 7.33 (t, J=8.2, 1H), 7.07 (d, J=8.8, 2H), 6.79 (d, J=8.3, 1H), 6.71-6.56 (m, 2H), 4.59 (s, 1H), 3.74 (s, 3H), 1.48 (d, J=7.2, 3H). $^{13}$C NMR (126 MHz, DMSO) δ 172.77, 166.62, 161.25, 160.15, 157.18, 131.21, 130.60, 128.27, 117.91, 111.73, 110.48, 105.86, 55.78, 47.98, 18.65.

Example 44

(R)-benzyl 2-tert-butoxy-1-cyanoethylcarbamate (30)

General procedure A was carried out with 1.5 g (9.3 mmol) of H-Ser(tBu)-OH and N-(Benzyloxycarbonyloxy)succinamide. Without further purification, general procedures B and C were performed. After flash chromatography, 1.67 g (6.045 mmol) of the title product was recovered as a clear oil. $^1$H NMR (500 MHz, CDCl$_3$) δ 7.36 (d, J=5.9, 4H), 5.14 (s, 2H), 4.12 (d, J=7.1, OH), 3.64 (d, J=9.2, 1H), 3.54 (dd, J=4.0, 9.3, 1H), 1.21 (s, 9H). $^{13}$C NMR (126 MHz, CDCl$_3$) δ 155.23, 135.56, 128.65, 128.52, 128.40, 117.86, 74.49, 67.75, 61.54, 43.63, 27.27, 14.20.

Example 45

Compound 31

General procedure E was used to deprotect 31 (1.4 mmol, 0.390 g) to yield 0.077 g (0.43 mmol) of the title product after recrystallization from methanol and diethyl ether. Most of the starting material was recovered from the reaction for later use. $^1$H NMR (500 MHz, CD$_3$OD) δ 4.66 (t, J=4.3, 1H), 3.80 (dd, J=2.9, 4.2, 2H), 1.28 (s, 10H). $^{13}$C NMR (126 MHz, CD$_3$OD) δ 114.37, 74.88, 59.41, 41.85, 26.05.

Example 46

(R)—N-(2-tert-butoxy-1-cyanoethyl)-4-octylbenzamide (32)

General procedure F was used to couple 0.43 mmol of 31 to 0.43 mmol of 2. After purification by flash chromatography 0.082 g (0.23 mmol) of the title product was recovered. $^1$H NMR (500 MHz, CDCl$_3$) δ 7.71 (d, J=8.0, 2H), 7.27 (d, J=8.0, 2H), 6.88 (d, J=8.6, 1H), 5.35-5.17 (m, 1H), 3.76 (dd, J=2.9, 9.3, 1H), 3.62 (dd, J=4.1, 9.3, 1H), 2.75-2.58 (m, 2H), 1.68-1.55 (m, 2H), 1.37-1.29 (m, 5H), 1.25 (d, J=0.6, 12H), 0.88 (t, J=6.8, 3H). $^{13}$C NMR (126 MHz, CDCl$_3$) δ 166.55, 147.98, 130.07, 128.81, 127.24, 117.76, 74.55, 61.66, 41.64, 35.87, 31.84, 31.17, 29.41, 29.22, 27.36, 22.64, 14.11.

Example 47

(R)-tert-butyl 1-amino-3-tert-butoxy-2-(4-octylbenzamido)-propylidenecarbamate (33)

General procedure I was used to convert 0.23 mmol (0.082 g) of 32. After column chromatography 0.052 g (0.11 mmol) was recovered as a clear oil. $^1$H NMR (500 MHz, CDCl$_3$) δ 7.74 (t, J=8.3, 2H), 7.32-7.22 (m, 2H), 7.12 (d, J=5.9, 1H), 4.76 (s, 1H), 4.00 (dd, J=4.2, 8.8, 1H), 3.44 (t, J=8.8, 1H), 2.73-2.57 (m, 2H), 1.61 (s, 2H), 1.51 (s, 9H), 1.35-1.19 (m, 19H), 0.87 (t, J=7.0, 3H). $^{13}$C NMR (126 MHz, CDCl$_3$) δ 169.66, 167.24, 148.96, 147.47, 130.83, 128.68, 128.59, 127.21, 127.13, 82.55, 77.27, 77.02, 76.76, 74.92, 62.48, 60.91, 53.66, 35.85, 31.84, 31.18, 29.41, 29.22, 28.22, 28.12, 27.95, 27.46, 27.32, 22.65, 14.11.

Example 48

VPC95139

General procedure J was used to deprotect 33 (0.11 mmol). The title product was recovered as a white solid; 7 mgs were recovered as an inseparable mixture of the title product and the corresponding amide. $^1$H NMR (500 MHz, CD$_3$OD) δ 8.98 (s, 1H), 8.71 (s, 1H), 8.47 (s, OH), 7.84 (dd, J=8.1, 25.9, 2H), 7.47-7.22 (m, 2H), 4.71 (s, 1H), 4.63 (s, 0H), 3.99 (s, 1H), 3.91 (s, 1H), 2.68 (d, J=7.8, 2H), 1.64 (s, 2H), 1.31 (d, J=19.9, 10H), 0.89 (t, J=7.0, 3H). $^{13}$C NMR (126 MHz, CD$_3$OD) δ 170.49, 169.18, 168.86, 148.01, 147.37, 131.33, 129.99, 128.31, 127.46, 61.77, 61.42, 55.61, 54.23, 47.57, 35.34, 31.59, 30.89, 29.28, 28.97, 22.29, 13.00.

Example 49

3-octylbenzaldehyde (34)

General procedure G was used to synthesize the title product starting with 1 g (5.4 mmol) of 3-bromobenzaldehyde. After flash chromatography, 0.725 g (3.3 mmol) of the desired product was recovered. $^1$H NMR (300 MHz, CDCl$_3$) δ 9.99 (s, 1H), 7.69 (dd, J=2.8, 4.8, 2H), 7.44 (dd, J=2.4, 4.1, 2H), 2.78-2.58 (m, 2H), 1.64 (dt, J=7.4, 15.1, 3H), 1.28 (dd, J=4.0, 15.8, 13H), 0.87 (t, J=6.8, 3H). $^{13}$C NMR (75 MHz, CDCl$_3$) δ 192.89, 144.21, 136.71, 134.95, 129.55, 129.10, 127.73, 35.86, 32.08, 31.51, 29.64, 29.45, 22.88, 14.33.

Example 50

3-octylbenzoic acid (35)

General procedure H was used to convert 34 into the title product. After standard work up and purification methods the title product was recovered in quantitative yield. $^1$H NMR (500 MHz, CDCl$_3$) δ 7.95 (s, 2H), 7.41 (dt, J=7.7, 15.6, 2H), 2.76-2.62 (m, 2H), 1.64 (dd, J=7.1, 14.8, 3H), 1.39-1.19 (m, 13H), 0.96-0.83 (m, 3H). $^{13}$C NMR (126 MHz, CDCl$_3$) δ 172.52, 143.38, 134.01, 130.08, 129.22, 128.38, 127.58, 60.69, 35.72, 31.87, 31.38, 29.44, 29.24, 22.67, 14.12.

Example 51

(S)—N-(1-cyanoethyl)-3-octylbenzamide (36)

General procedure D was used to deprotect 1.15 mmol of 4 and was then immediately coupled to 1.15 mmol of 35. After flash chromatography 0.115 g (0.4 mmol) of the title product was recovered. $^1$H NMR (500 MHz, CDCl$_3$) δ 7.68-7.55 (m, 2H), 7.34 (dd, J=2.9, 9.5, 2H), 6.73 (d, J=7.7, 1H), 5.16 (p, J=7.2, 1H), 2.63 (t, J=7.7, 2H), 1.66 (d, J=7.2, 2H), 1.61 (s, 2H), 1.30 (dd, J=21.4, 28.1, 10H), 0.87 (t, J=7.0, 3H). $^{13}$C NMR (126 MHz, CDCl$_3$) δ 166.89, 143.81, 143.59, 132.58, 132.52, 128.60, 127.34, 124.32, 119.40, 52.60, 48.47, 36.28, 35.81, 31.86, 31.43, 31.38, 29.42, 29.27, 29.23, 22.66, 19.54, 18.65, 14.11.

Example 52

(S)-tert-butyl 1-amino-2-(3-octylbenzamido)propylidenecarbamate (37)

General procedure I was used to convert 0.4 mmol of 36 to the title product. After column chromatography 0.1 mmol (0.042 g) was recovered. $^1$H NMR (500 MHz, CDCl3) δ 9.19 (s, 1H), 7.62 (d, J=8.4, 3H), 7.41 (s, 1H), 7.40-7.30 (m, 2H), 4.97-4.82 (m, 1H), 2.69-2.60 (m, 2H), 1.66-1.58 (m, 2H), 1.56 (d, J=6.9, 3H), 1.53-1.47 (m, 9H), 1.39-1.14 (m, 11H), 0.87 (t, J=7.0, 3H). $^{13}$C NMR (126 MHz, CDCl$_3$) δ 172.73, 167.56, 143.51, 133.56, 131.97, 128.41, 127.22, 124.51, 79.83, 49.91, 35.84, 31.86, 31.45, 29.43, 29.32, 29.23, 28.13, 27.96, 22.64, 19.61, 14.11.

Example 53

VPC95151

General procedure K was used to deprotect 0.1 mmol of 37. Standard purification techniques were employed. $^1$H NMR (500 MHz, CD$_3$OD) δ 8.71 (s, 1H), 7.74 (d, J=13.6, 2H), 7.37 (s, 2H), 4.63 (s, 1H), 2.65 (s, 2H), 1.61 (s, 5H), 1.28 (d, J=26.5, 10H), 0.85 (s, 3H). $^{13}$C NMR (126 MHz, CD$_3$OD) δ 173.18, 169.38, 143.26, 132.51, 132.20, 128.21, 127.50, 124.88, 35.43, 31.62, 31.25, 29.18, 28.99, 22.32, 17.39, 13.07.

Example 54

3-(benzyloxy)phenol (38)

To a stirring solution of resorcinol (58 mmol, 6.4 g) in acetonitrile (25 mL) was added potassium carbonate (5.8 mmol, 0.801 g). The solution was then heated to reflux for 1 hour. At this time, benzyl bromide (5.8 mmol, 1 g) in acetonitrile (33 mL) was added to the refluxing mixture. The reaction was monitored by TLC until all benzyl bromide was consumed. At this time the reaction mixture was cooled to room temperature and filtered through a fitted funnel. The mother liquor was then evaporated to an oil and taken up in ethyl acetate (200 mL). The organic layer was extracted with three 15 mL portions of aqueous 1N HCl followed by one 10 mL portion of brine. The organic layer was dried over magnesium sulfate and evaporated to dryness. The crude mixture was purified via flash chromatography to yield 0.819 g (4.1 mmol) of the title product. $^1$H NMR (300 MHz, CDCl$_3$) δ 7.57-7.33 (m, 5H), 7.15 (t, J=8.2, 1H), 6.59 (dd, J=2.0, 7.9, 1H), 6.52-6.41 (m, 2H), 5.10 (s, 1H), 5.03 (s, 2H). $^{13}$C NMR (75 MHz, CDCl$_3$) δ 160.70, 156.84, 137.04, 130.48, 128.86, 128.29, 127.79, 108.36, 107.66, 102.72, 70.29.

Example 55

4-(3-(benzyloxy)phenoxy)benzaldehyde (39)

To a stirring solution of p-fluorobenzaldehyde (6.15 mmol, 0.763 g) in dimethylformamide (20.5 mL) was added cesium carbonate (4.1 mmol, 1.33 g) and 38 (4.1 mmol, 0.819 g). This solution was heated to 90° C. and monitored with TLC. When complete, the reaction mixture was cooled to room temperature and filtered through a fritted funnel. The filtrate was then diluted with ethyl acetate (200 mL) and extracted with eight 15 mL portions of water and one 10 mL portion of brine. The organic layer was dried over magnesium sulfate, evaporated to dryness and purified with flash chromatography to yield 0.930 g (3.05 mmol) of the title product. $^1$H NMR (500 MHz, CDCl$_3$) δ 9.93 (s, 1H), 7.85 (d, J=8.6, 2H), 7.55-7.22 (m, 6H), 7.07 (d, J=8.7, 2H), 6.86 (d, J=8.3, 1H), 6.71 (dd, J=5.2, 10.7, 2H), 5.06 (s, 2H). $^{13}$C NMR (126 MHz, CDCl$_3$) δ 190.79, 162.93, 160.50, 156.39, 131.94, 130.61, 128.66, 128.15, 127.52, 117.78, 112.66, 111.44, 107.25, 70.18.

Example 56

4-(3-(benzyloxy)phenoxy)benzoic acid (40)

General procedure H was used to convert 3.05 mmols of 39 into the title product. No purification beyond that described in the general procedure was carried out. $^1$H NMR (300 MHz, CDCl$_3$) δ 8.07 (d, J=8.9, 2H), 7.51-7.21 (m, 6H), 7.01 (d, J=8.9, 2H), 6.83 (d, J=8.5, 1H), 6.68 (d, J=7.8, 2H), 5.05 (s, 2H).

Example 57

(S)-4-(3-(benzyloxy)phenoxy)-N-(1-cyanoethyl) benzamide (41)

General procedure D was used to deprotect 0.65 mmol of 4 and immediately coupled to 0.975 mmol of 40. After flash chromatography 0.96 g (0.25 mmol) of the title product was recovered. $^1$H NMR (300 MHz, CDCl$_3$) δ 7.76 (d, J=8.8, 2H), 7.49-7.21 (m, 6H), 7.00 (d, J=8.7, 2H), 6.80 (d, J=8.3, 1H), 6.65 (d, J=12.0, 3H), 5.22-5.08 (m, 1H), 5.03 (s, 2H), 1.65 (d, J=7.2, 3H).

Example 58

(S)-tert-butyl 1-amino-2-(4-(3-(benzyloxy)phenoxy) benzamido)-propylidenecarbamate (42)

General procedure I was used to convert 0.25 mmol of 41 to the title product. After flash chromatography 0.042 g (0.1 mmol) of the title product was recovered. $^1$H NMR (500 MHz, CDCl$_3$) δ 7.81 (d, J=7.9, 2H), 7.48-7.17 (m, 7H), 7.01 (d, J=8.7, 2H), 6.81 (d, J=8.3, 1H), 6.73-6.59 (m, 2H), 5.05 (s, 2H), 4.84 (s, 1H), 1.62-1.39 (m, 13H). $^{13}$C NMR (126 MHz, CDC13) δ 166.54, 160.45, 160.15, 157.06, 136.53, 130.43, 129.20, 129.15, 128.62, 128.08, 127.50, 117.97, 112.04, 110.85, 106.57, 70.14, 49.89, 49.56, 28.14, 27.98, 19.61, 18.05.

Example 59

VPC95157

General procedure J was used to deprotect 0.1 mmol of 42 to produce the title product. Hydrochloric acid in diethyl ether was not added to the product and was thus recovered as the trifluoroacetate salt; the final product was submitted as an inseparable mixture with the corresponding amide. $^1$H NMR (500 MHz, CD$_3$OD) δ 7.93 (d, J=8.8, 1H), 7.86 (d, J=8.8, 1H), 7.48-7.24 (m, 5H), 7.07-6.94 (m, 2H), 6.85 (d, J=8.3, 1H), 6.65 (d, J=32.6, 2H), 5.07 (s, 2H), 4.64 (d, J=7.3, 1H), 4.55 (s, OH), 1.62 (d, J=7.2, 2H), 1.47 (d, J=7.2, 1H). $^{13}$C NMR (126 MHz, CD$_3$OD) δ 173.05, 168.82, 161.08, 160.17, 156.95, 137.03, 130.24, 129.56, 129.21, 128.11, 127.54, 127.16, 117.22, 111.76, 110.77, 106.60, 69.73, 16.80.

The assays below are standard literature reported assays known in the art for confirming and quantifying the activity of the disclosed compounds.

Example 60

Sphingosine Kinase Assay

High levels of mouse sphingosine kinase type 1 (mSK1) and mouse sphingosine kinase type 2 (mSK2) were expressed in HEK293T cells by transfection with their cognate cDNAs.

Crude homogenates were incubated with γ-[$^{33}$P]ATP and different concentrations of D-erythro-sphingosine in the presence of 0, 30, 100 or 300 micromolar of test compound VPC94075 for 0.5 hour at 37 C. The product, radiolabeled S1P, was isolated by binding to plastic plates containing a scintillant. The bound product was detected by proximity scintillation counting. The results are illustrated in FIGS. 14 and 15.

Example 61

Sphingosine Kinase Competition Assay

Figure 17:
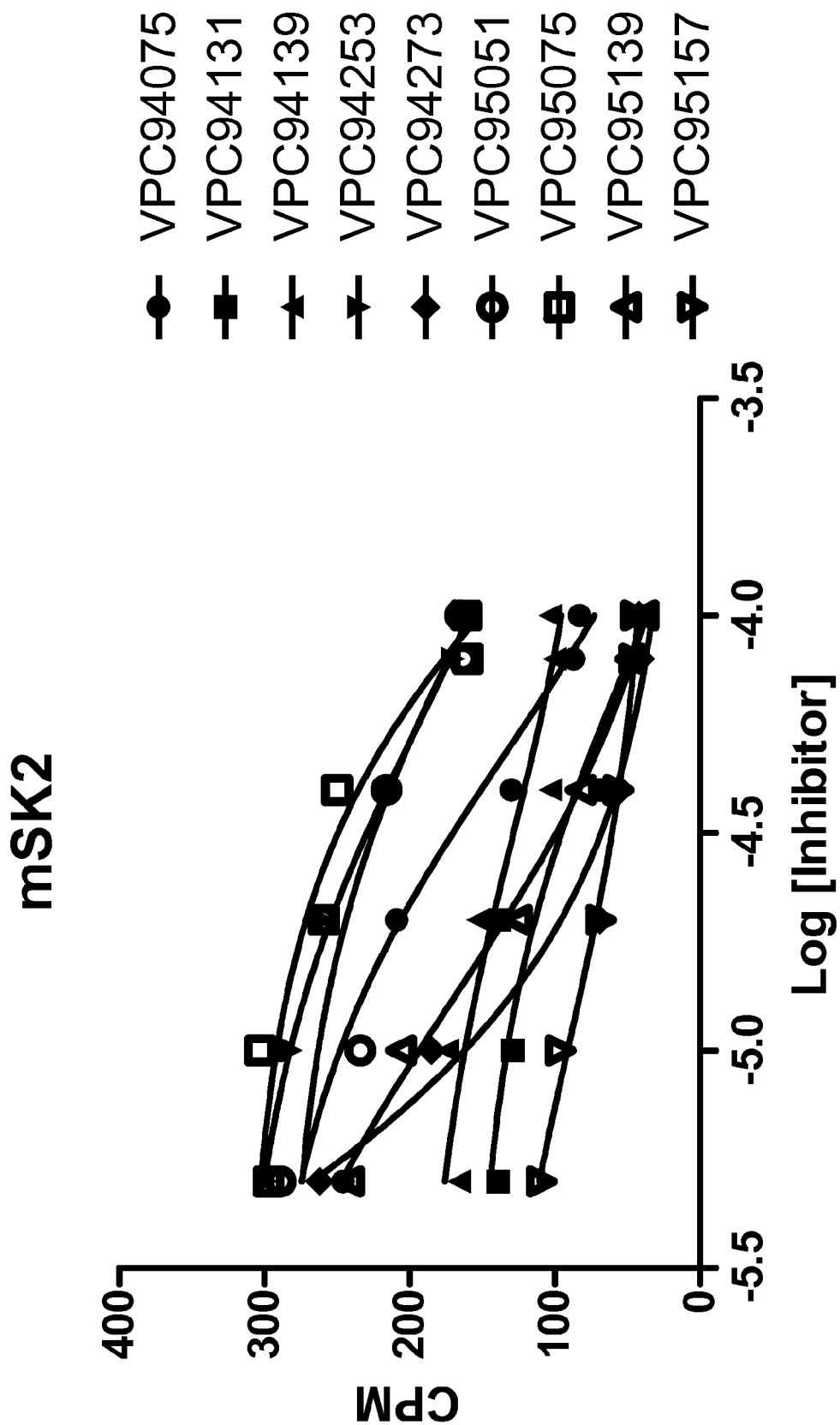

Sphingosine kinase activity was assessed as described previously (Kharel, Y., Lee, S., Snyder, A. H., Sheasley-O'Neill, S. L., Morris, M. A., Setiady, Y., Zhu, R., Zigler, M. A., Burcin, T. L., Ley, K., Tung, K. S. K., Engelhard, V. H., Macdonald, T. L. and Lynch, K. R. Sphingosine kinase 2 is required for modulation of lymphocyte traffic by FTY720. *J Biological Chemistry* 280: 36865-36872 (2005)). High levels of mouse sphingosine kinase type 1 (mSK1) and mouse sphingosine kinase type 2 (mSK2) were expressed in HEK293T cells by transfection with their cognate cDNAs. Crude homogenates were incubated with γ-[$^{32}$P]ATP and 1 micromolar D-erythro-sphingosine for 0.5 hour at 37 C. The product, radiolabeled S1P, was isolated by thin layer chromatography, recovered and radioactivity measured by liquid scintillation counting. Concentrations of inhibitor test compounds, VPC94075, VPC94131, VPC94253, VPC94273, VPC95051, VPC95075, VPC95139 and VPC95157, were 5, 10, 20, 40, 80 or 100 micromolar. The results are illustrated in FIGS. 16 and 17.

Example 62

Sphingosine S1P reduction

Figure 18:
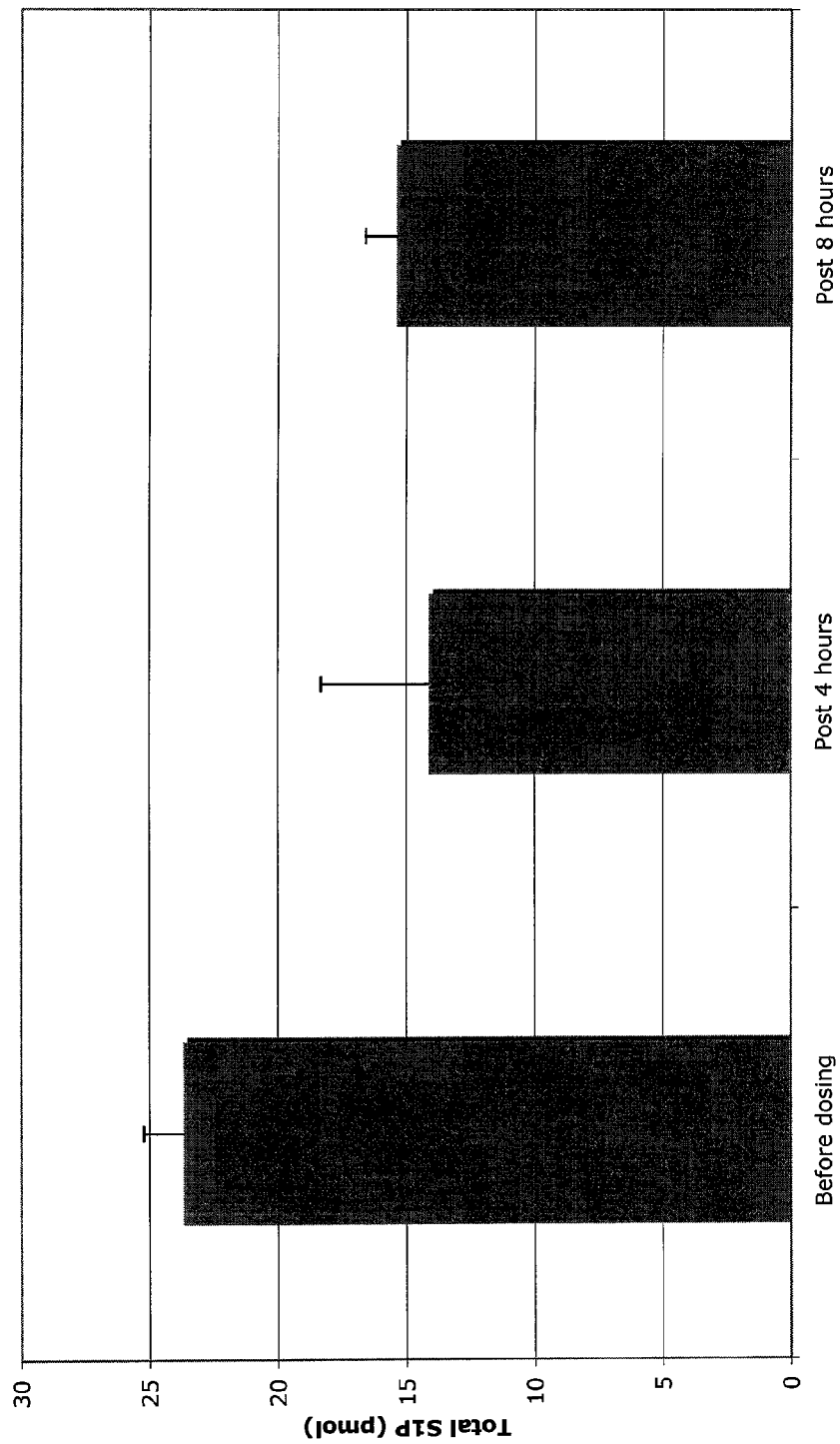
FIG. 18 illustrates the results of the in vivo Sphingosine S1P reduction using VPC94075.

Mice (five animals) were injected i.p. with 20 mg/kg of test compound, VPC94075, dissolved in 2% hydroxypropyl-beta-cyclodextrin containing 5% DMSO. Blood was drawn from the orbital sinus at the times indicated, plasma was prepared by LC-MS-MS after bis-acetylation as described (E. V. Berdyshev, I. A. Gorshkova, J. G. N. Garcia, V. Natarajan, W. C. Hubbard (2005) Quantitative analysis of sphingoid base-1-phosphates as bis-acetylated derivatives by liquid chromatography-tandem mass spectrometry. *Analytical Biochemistry* 339: 129-136). The average S1P levels (pmol) from mouse plasma before and after a single dose of VPC94075 are illustrated in FIG. 18.

Example 63

Smooth Muscle Cell Growth Inhibition

Figure 19:
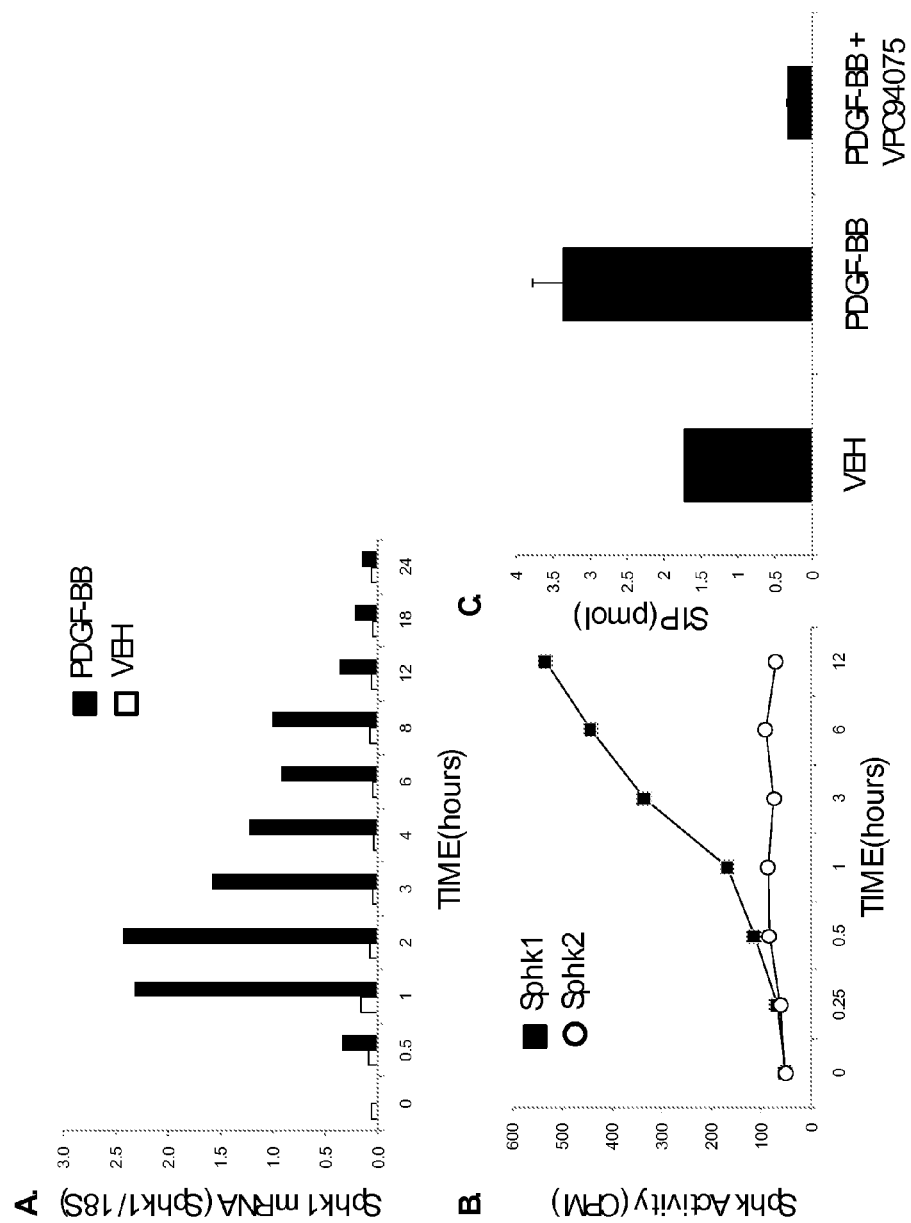
FIGS. 19A, 19B, and 19C illustrate the results of the smooth muscle cell growth inhibition assay.

Smooth muscle cells (SMCs) are treated with platelet-derived growth factor BB (PDGF-BB), a potent modulator of SMC. As shown in FIG. 19, treatment of SMCs in vitro with PDGF-BB (30 ng/ml) resulted in 1) a transient increase in SphK1 mRNA levels (Q-RTPCR) (FIG. 19A), 2) an increase in SphK activity (P$^{32}$ ATP kinase assay) that was predominantly the Sphk1 isoform, not Sphk2, (FIG. 19B) and 3) an increase in S1P production (LC/MS) (FIG. 19C).

FIG. 19 illustrates the PDGF-BB increase Sphk1 mRNA, Spkh1 (not Sphk2) activity and S1P production. Test compound VPC94075 prevents PDFD-BB-induced Sphk1 activity. Cultured rat aortic smooth muscle cells were stimulated with PDGF-BB. 19A.) Real-time PCR analysis of Sphk1 mRNA at various time points compared to vehicle control. 19B.) Analysis of Sphk1 and Sphk2 activity (P$^{32}$ATP kinase assay). 19C.) S1P concentration in the media 12 hours after stimulating SMCs with PDGF-BB. Test compound VPC94075 (10 uM) blocks PDGF-BB-induced S1P production.

Example 64

SphK1 Activity in Arteries following Balloon Injury In Vivo

Rats (300-325 g) underwent angioplasty balloon-induced injury of the left common carotid artery using a 2F Fogarty catheter. Briefly, the 2F Fogarty balloon catheter is introduced through an arteriotomy in the external carotid of the left common carotid artery and placed proximal to the aortic arch. The balloon is inflated with 0.2 ml of saline and pulled back towards the arteriotomy. This repeated 3 times and the external carotid is tied off distal and proximal to the arteriotomy, blood flow is restored and the incision is closed. This is a routinely used model in the field that mimics high smooth muscle cell proliferation rates and neointimal hyperplasia associated with balloon angioplasty in humans. In this study, animals were euthanized 3 and 7 post injury (N=3 rats per time point). SphK1 activity was measured in injured and uninjured arteries by P$^{32}$ ATP kinase assay.

Figure 20:
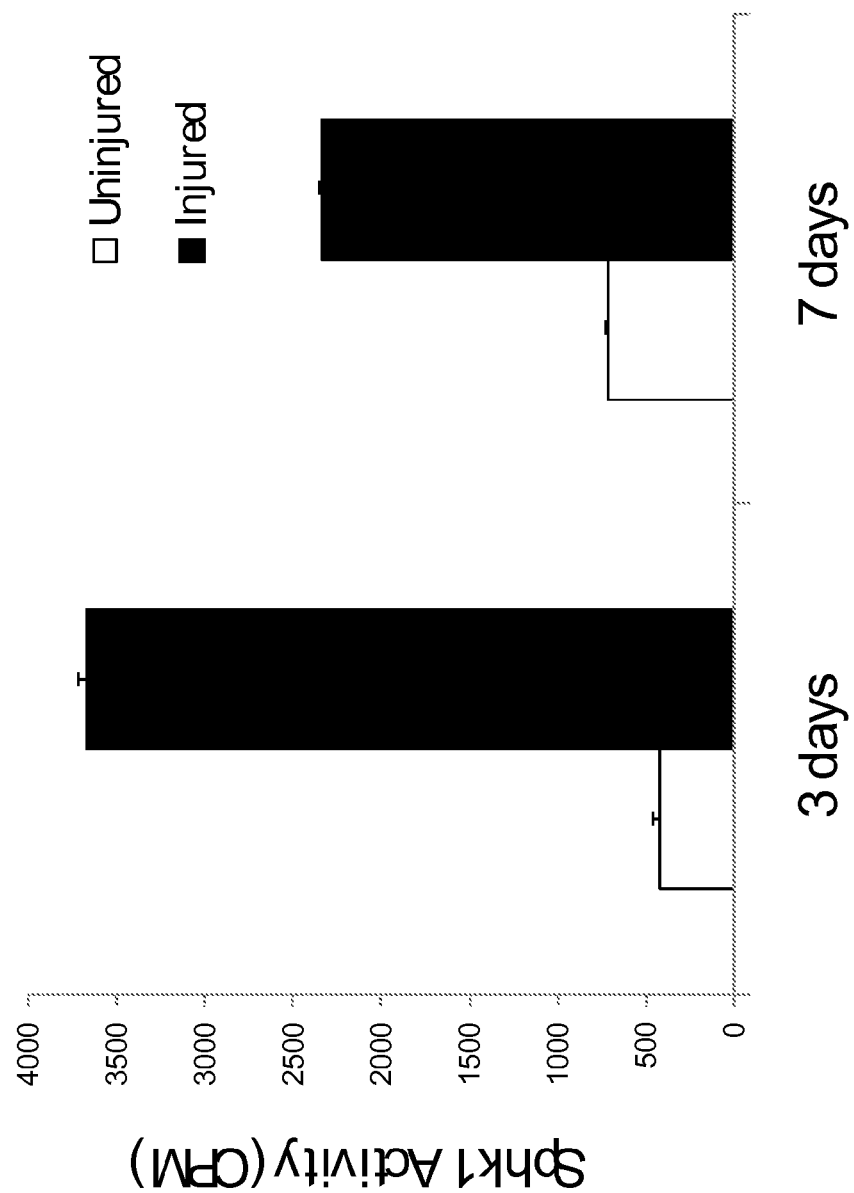
FIG. 20 illustrates the SphK1 activity in arteries following a balloon injury in vivo using the disclosed compounds.

In FIG. 20, acute balloon injury of the rat carotid artery resulted in increased SphK1 mRNA levels and SphK1 activity at 3 and 7 days post-injury is shown. The early induction of Spk1 activity 3 days (FIG. 20) is synonymous with high smooth muscle cell proliferation rates associated with balloon angioplasty-induced neointimal hyperplasia.

Example 65

Prevention of PDGF-BB-Induced SMC Proliferation

Cells were treated with a non-selective SphK inhibitor VPC94075 (suppresses both endogenous and PDGF-BB-induced S1P production). Cell proliferation was measured by BrdU incorporation. (VPC94193 is an inactive form of VPC94075) Inhibition of SphK with VPC94193 (a non-active form) prevented PDGF-BB-induced SMC proliferation (FIG. 21A).

Cell cytoxicity was measured by Promega caspase activity assay (CsA at 10 uM is toxic dose in SMCs, control). VPC94075 does not induce cell death after 24 hr treatment (See FIG. 21B). Images of SMCs treated with and without VPC94075 showing healthy cell morphology and prevention of SMC proliferation as indicated by differences in confluence. See FIG. 21C.

All references cited herein are expressly incorporated herein by reference in their entirety into this disclosure. The invention should not be construed to be limited solely to the assays and methods described above, but should be construed to include other methods and assays as well. Other methods that are used but not described above are well known and within the competence of one of ordinary skill in the art of chemistry, biochemistry, molecular biology, and clinical medicine. One of ordinary skill in the art will know that other assays and methods are available to perform the procedures described above.

The abbreviations used above have their conventional meaning within the clinical, chemical, and biological arts. In the case of any inconsistencies, the present disclosure, including any definitions therein will prevail.

We claim:

1. A compound of Formula IA:

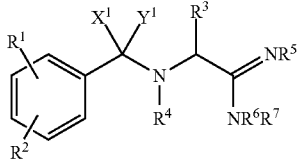

wherein $X^1$ and $Y^1$ are independently hydrogen or $(C_1$-$C_4)$alkyl; or $X^1$ and $Y^1$ taken together are O or S;

$R^1$ is benzyl, phenylethyl, benzyl substituted with methyl, $(C_6$-$C_{12})$alkyl, or $(C_5$-$C_{11})$alkoxy, and $R^2$ is hydrogen, halo, halo$(C_1$-$C_{10})$alkyl, cyano, —$NR^aR^b$, $(C_1$-$C_{20})$alkyl, $(C_2$-$C_{20})$alkenyl, $(C_2$-$C_{20})$alkynyl, $(C_1$-$C_{20})$alkoxy, $(C_2$-$C_{26})$alkoxyalkyl, $(C_3$-$C_{12})$cycloalkyl, $(C_6$-$C_{10})$aryl, $(C_7$-$C_{30})$arylalkyl, $(C_2$-$C_{10})$heterocyclic, $(C_4$-$C_{10})$heteroaryl, or $(C_4$-$C_{10})$heteroaryl$(C_1$-$C_{20})$alkyl; or $R^1$ is hydrogen and $R^2$ can be a group having formula II, III, IV, V, or VI;

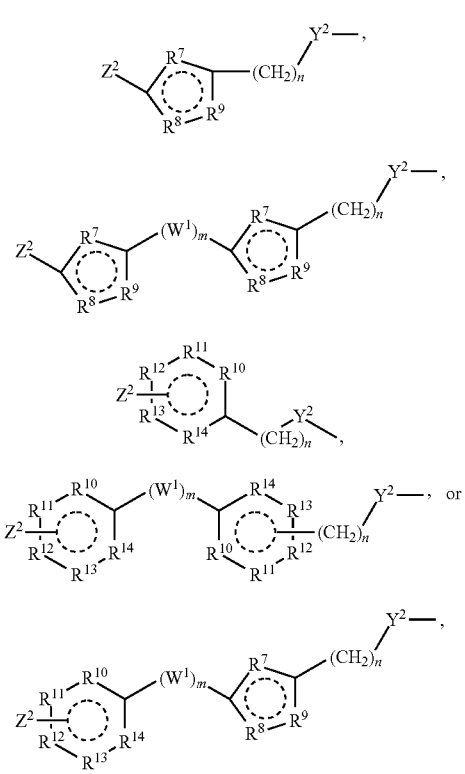

wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{18}$;

each $R^{15}$, $R^{16}$ and $R^{17}$ is independently hydrogen, halo, $(C_1$-$C_{10})$alkyl, $(C_6$-$C_{10})$aryl, $(C_1$-$C_{10})$alkyl substituted with halo, hydroxy, $(C_1$-$C_{10})$alkoxy, or cyano; and where $R^{18}$ can be hydrogen or $(C_1$-$C_{10})$alkyl;

where $Z^2$ is hydrogen, halo, halo$(C_1$-$C_{10})$alkyl, cyano, —$NR^cR^d$, $(C_1$-$C_{20})$alkyl, $(C_2$-$C_{20})$alkenyl, $(C_2$-$C_{20})$alkynyl, $(C_1$-$C_{20})$alkoxy, $(C_2$-$C_{26})$alkoxyalkyl, $(C_3$-$C_{12})$cycloalkyl, $(C_6$-$C_{10})$aryl, $(C_7$-$C_{30})$arylalkyl, $(C_2$-$C_{10})$heterocyclic, $(C_4$-$C_{10})$heteroaryl, or $(C_4$-$C_{10})$heteroaryl$(C_1$-$C_{20})$alkyl;

wherein the alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, $(C_1$-$C_{10})$alkoxy, $C_6$-aryl, $(C_7$-$C_{24})$arylalkyl, oxo (=O), or imino (=$NR^f$), wherein one or more of the carbon atoms in the $Z^2$ alkyl groups can be independently replaced with non-peroxide oxygen, sulfur or $NR^e$;

wherein $Y^2$ is a bond, O, S, C=O, or $NR^e$, $CH_2$; $W^1$ is a bond, —$CH_2$— and m is 1, 2, or 3, or (C=O)$(CH_2)_{1\text{-}5}$ and m is 1; wherein $W^1$ is optionally interrupted with non-peroxide O, S, C=O, or $NR^e$;

indicates one or more optional double bonds; and n is 0, 1, 2, or 3;

$R^3$ is hydrogen, $(C_1$-$C_4)$alkyl, hydroxy$(C_1$-$C_3)$alkyl, $(C_1$-$C_3)$alkoxy or halo$(C_1$-$C_3)$alkyl;

each $R^4$, $R^5$, $R^6$ and $R^7$ is independently hydrogen, $(C_1$-$C_4)$alkyl or halo$(C_1$-$C_3)$alkyl;

wherein the alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, $(C_1$-$C_{10})$alkoxy, $C_6$-aryl, $(C_7$-$C_{24})$arylalkyl, oxo (=O), or imino (=$NR^f$), wherein one or more of the carbon atoms in the $R^1$ or $R^2$ alkyl groups can be independently replaced with non-peroxide oxygen, sulfur or $NR^e$; and each $R^a$, $R^b$, $R^c$, $R^d$, $R^e$ and $R^f$ is independently hydrogen, or $(C_1$-$C_{10})$alkyl; or a pharmaceutically acceptable salt thereof.

2. The compound of claim 1, wherein $X^1$ and $Y^1$ are O.

3. The compound of claim 1, wherein $R^2$ is $(C_1$-$C_{20})$alkyl, or $(C_1$-$C_{20})$alkoxy.

4. The compound of claim 3, wherein $R^2$ is $(C_1$-$C_{10})$alkyl, $(C_2$-$C_{10})$alkenyl and $(C_2$-$C_{14})$alkynyl or $(C_1$-$C_{10})$alkoxy optionally substituted with carbonyl (C=O) or oxime (C=$NR^d$) groups.

5. The compound of claim 4, wherein $R^2$ is methyl, ethyl, propyl, butyl, pentyl, hexyl, heptyl, octyl, nonyl, decyl, trifluoromethyl, trifluoroethyl, trifluoromethoxy, trifluoroethoxy, methoxy, ethoxy, propoxy, butoxy, pentoxy, heptoxy, octoxy or nonoxy.

6. The compound of claim 1, wherein $R^2$ is:

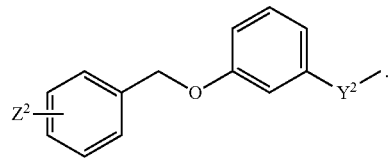

7. The compound of claim 6, wherein $Y^2$ is O and $Z^2$ is hydrogen or $(C_1$-$C_{10})$alkyl.

8. The compound of claim 1, wherein $R^2$ is

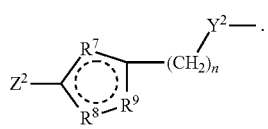

9. The compound of claim 8, wherein $R^2$ is:

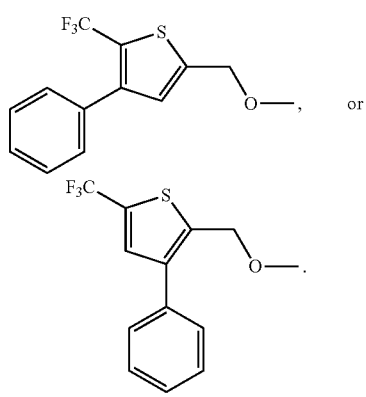

10. The compound of claim 9, wherein $R^2$ is

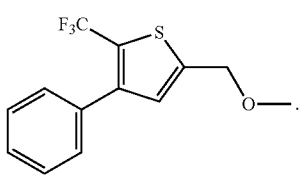

11. The compound of claim 1, wherein $R^2$ is:

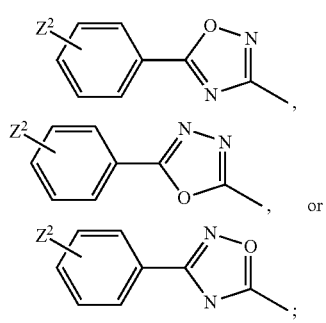

wherein $Z^2$ is $(CH_3)_3C-$, $CH_3CH_2(CH_3)_2C-$, $CH_3CH_2CH_2-$, $CH_3(CH_2)_2CH_2-$, $CH_3(CH_2)_4CH_2-$, $(CH_3)_2CHCH_2-$, $(CH_3)_3CCH_2-$, $CH_3CH_2O-$, $(CH_3)_2CHO-$, or $CF_3CH_2CH_2-$ or a group having the formula:

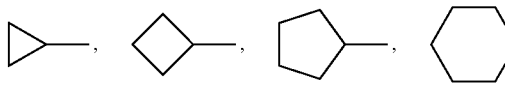

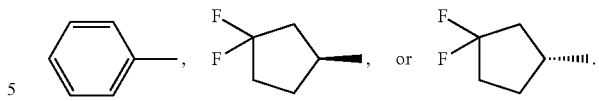

12. The compound of claim 11, wherein R is:

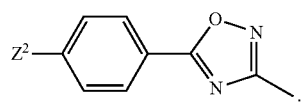

13. The compound of claim 12, wherein $R^2$ is:

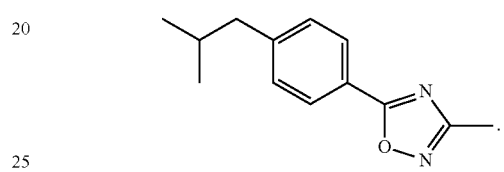

14. The compound of claim 1, wherein $R^2$ is:

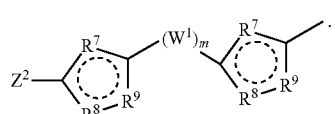

15. The compound of claim 14, wherein $R^2$ is

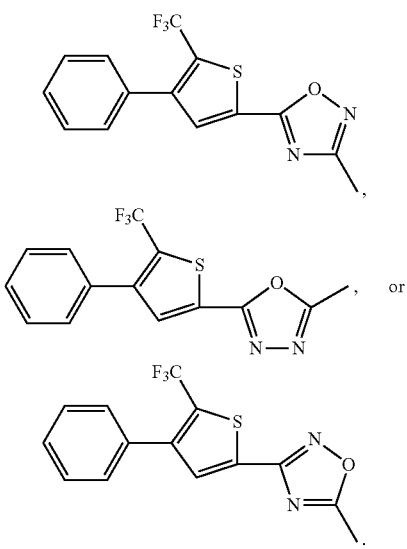

16. The compound of claim 1, wherein $R^3$ is hydrogen, methyl, hydroxymethyl, ethyl, hydroxyethyl, n-propyl, or isopropyl.

17. The compound of claim 16, wherein $R^3$ is hydrogen, methyl, hydroxymethyl, ethyl, or hydroxyethyl.

18. The compound of claim 1, having the formula
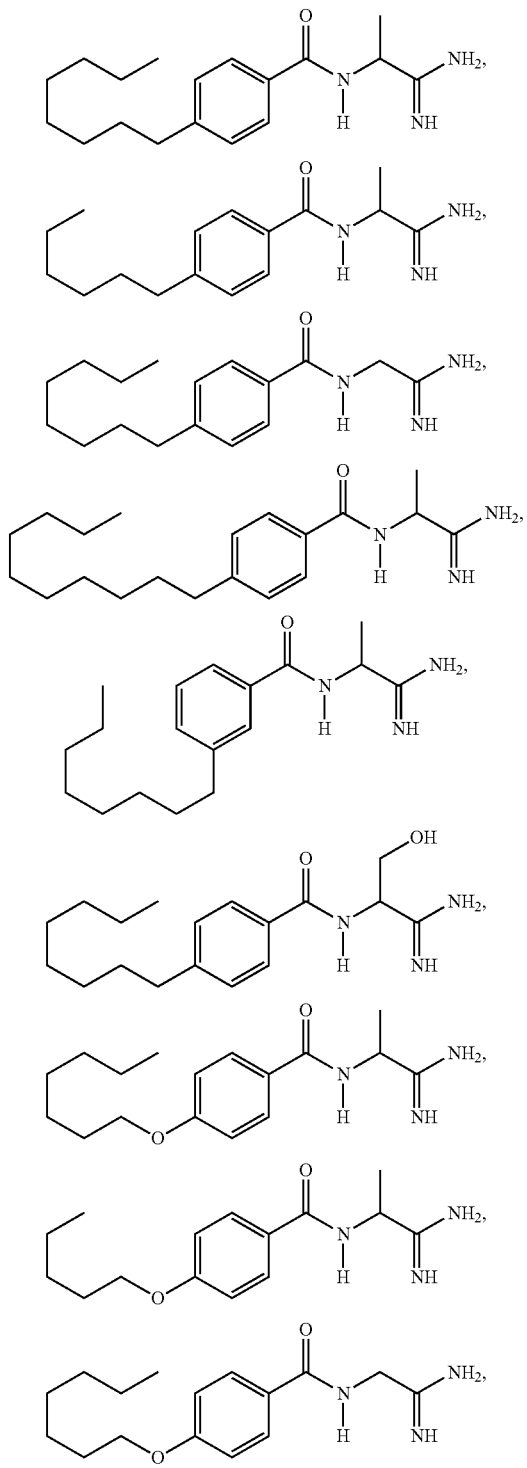
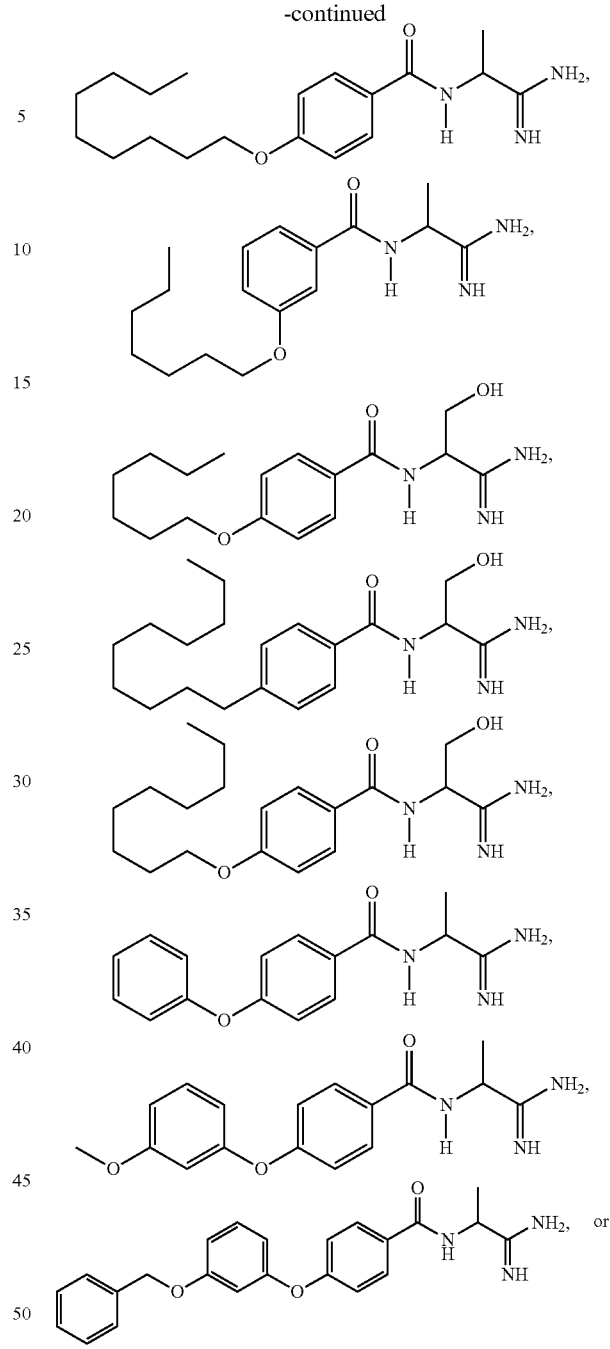
a salt thereof.
19. A pharmaceutical composition comprising a compound having the formula of claim 1, and a pharmaceutically acceptable carrier.
20. The composition of claim 19, wherein the composition is in the form of a kit.
* * * * *